United States Patent
Grendze et al.

(10) Patent No.: US 6,395,179 B1
(45) Date of Patent: May 28, 2002

(54) THERMALLY-MANAGED SEPARATION AND DEWATERING PROCESSES FOR RECOVERING ACID PRODUCTS

(75) Inventors: Martin Grendze, Indianapolis, IN (US); Frank Verhoff, Cincinnati, OH (US)

(73) Assignee: Reilly Industries, Inc., Indianapolis, IN (US)

(*) Notice: Subject to any disclaimer, the term of this patent is extended or adjusted under 35 U.S.C. 154(b) by 54 days.

(21) Appl. No.: 09/648,265

(22) Filed: Aug. 25, 2000

Related U.S. Application Data

(62) Division of application No. 08/699,532, filed on Aug. 19, 1996, now Pat. No. 6,146,534.

(51) Int. Cl.[7] .............................................. B01D 15/08
(52) U.S. Cl. ...................... 210/635; 210/656; 210/659; 562/580; 562/582; 562/584
(58) Field of Search ................. 562/580, 582, 562/584; 210/635, 656, 659, 198.2

(56) References Cited

U.S. PATENT DOCUMENTS

| | | | |
|---|---|---|---|
| 4,323,702 A | 4/1982 | Kawabata et al. | 562/485 |
| 4,522,726 A | 6/1985 | Berry et al. | 210/660 |
| 4,552,905 A | 11/1985 | Keil et al. | 521/149 |
| 4,720,579 A | 1/1988 | Kulprathipanja | 562/580 |
| 4,764,276 A | 8/1988 | Berry et al. | 210/264 |
| 4,808,317 A | 2/1989 | Berry et al. | 210/660 |
| 4,851,573 A | 7/1989 | Kulprathipanja et al. | 562/580 |
| 4,851,574 A | 7/1989 | Kulprathipanja | 562/580 |
| 5,032,686 A | 7/1991 | Duflot et al. | 562/580 |
| 5,382,681 A | 1/1995 | Derez et al. | 562/580 |
| 5,412,126 A | 5/1995 | King et al. | 554/185 |

FOREIGN PATENT DOCUMENTS

| | | | |
|---|---|---|---|
| WO | WO 92/16490 | 10/1992 | 562/580 |
| WO | Wo 92/16534 | 10/1992 | 562/580 |
| WO | WO 93/06226 | 4/1993 | 562/580 |
| ZA | 85 5155 | 7/1985 | 562/580 |

*Primary Examiner*—Ernest G. Therkorn
(74) *Attorney, Agent, or Firm*—Woodard, Emhardt, Naughton, Moriarty & McNett

(57) ABSTRACT

Described are preferred processes separating desired chemical products from impurities in solution utilizing thermally-managed chromatography over solid adsorbents. The preferred processes involve chromatographic principles which are assisted by varying the temperature of operation in separation and elution phases. Also described are processes for treating aqueous acids to dewater and recover the acids in an organic solvent such as an alcohol.

7 Claims, 20 Drawing Sheets

THERMALLY-MANAGED SEPARATION AND DEWATERING PROCESSES FOR RECOVERING ACID PRODUCTS

CROSS-REFERENCE TO RELATED APPLICATIONS

This application is a divisional of prior application Ser. No. 08/699,532, filed on Aug. 19, 1996, now U.S. Pat. No. 6,146,534.

BACKGROUND OF THE INVENTION

The present invention relates generally to techniques for recovering valuable chemical products. More particularly, the invention relates to highly efficient and economic processes for selectively recovering desired products from liquid mediums in which they are contained along with impurities, involving novel thermally-assisted chromatographic techniques.

As further background, the recovery and purification of acidic compounds such as carboxylic acids and other valuable chemical products from mediums has long been studied in an effort to discover efficient, cost-effective routes for their production. For example, carboxylic acids such as citric acid and lactic acid are manufactured by fermentation in large scale worldwide. Such fermentations provide fermentation broths from which the desired acid must be recovered and purified. Where high volume manufacture is involved, the importance of keeping recovery costs to a minimum cannot be overemphasized.

Recent recovery work has focused on the use of solid polymeric adsorbent materials to recover carboxylic acids from fermentation mediums. In this approach, the fermentation broth is passed over the adsorbent which adsorbs the carboxylic acid, and the carboxylic acid is desorbed in some fashion to provide product. Generally, a wide variety of adsorbents and adsorption/desorption schemes have been proposed.

For example, Kawabata et al., in U.S. Pat. No. 4,323,702, describe a process for recovering carboxylic acids with a material of which the main component is a polymeric adsorbent having a pyridine skeletal structure and a cross-linked structure. The carboxylic acid is adsorbed on the adsorbent, and then desorbed using a polar organic material such as an aliphatic alcohol, ketone or ester.

Kulprathipanja et al., in U.S. Pat. Nos. 4,720,579, 4,851,573, and 4,851,574, teach solid polymeric adsorbents including a neutral, noniogenic, macroreticular, water-insoluble cross-linked styrene-poly(vinyl)benzene, a cross-linked acrylic or styrene resin matrix having attached tertiary amine functional groups or pyridine functional groups, or a cross-linked acrylic or styrene resin matrix having attached aliphatic quaternary amine functional groups. In their work, Kulprathipanja et al. describe "pulse tests" conducted under isothermal conditions in which they identify acetone/water, sulfuric acid, and water as desorbents.

South African Patent Application No. 855155, filed Jul. 9, 1985, describes processes in which product acids were recovered from their aqueous solutions. In the adsorption step, the acid-containing solution was passed through a column containing an adsorber resin consisting of a vinylimidazole/methylene-bis-acrylamide polymer, a vinylpyridine/trimethylolpropane trimethacrylate/vinyltrimethylsilane polymer, a vinylimidazole/N-vinyl-Nmethylacetamide/methylene-bis-acrylamide polymer, Amberlite IRA 35 (Rohm & Haas—acrylate/divinylbenzene based polymer containing dimethylamino groups), or Amberlite IRA 93 SP (Rohm & Haas) or Dowex MWA-1 or WGR-2 (Dow Chemical) (these latter three being styrene/divinylbenzene based polymers containing dimethylamino groups). To desorb the acid, water, usually at a temperature of 90° C., was allowed to pass through the column. However, the single-pass elution process described involves an inefficient use of heat energy and does not substantially maximize the potential use of the resins to achieve highly concentrated desorbed solutions. Additionally, resins employed in this South African application are relatively thermally unstable and thus substantially degrade during desorption procedures employing hot water.

International Applications PCT/US92/02107 filed Mar. 12, 1992 (published Oct. 1, 1992, WO 92/16534) and PCT/US92/01986 filed Mar. 12, 1992 (published Oct. 1, 1992, WO 92/16490) both by Reilly Industries, Inc., disclose desorbing lactic and citric acid, respectively, from divinylbenzene crosslinked vinylpyridine or other resins using steam or hot water. The resins employed have advantageous adsorption/desorption capacities and are highly thermally stable under the described hot water desorption procedures. Nonetheless, improved processes would provide greater efficiency in the use of the resins and of heat applied to the desorption, and would readily provide desorbed solutions of even higher product concentration.

Still further processes for recovering acid products have been reported. For instance, U.S. Pat. No. 5,412,126 describes processes in which citric acid is adsorbed on a base resin and then stripped using an alkylamine. The free acid is then recovered by dewatering the material and driving the amine off with heat. U.S. Pat. No. 5,032,686 describes a process in which citric acid is separated from sugars using an acid resin, whereas U.S. Pat. No. 5,382,681 describes a process in which an impurity-containing citric acid solution is first treated with base to convert the citric acid to trisodium citrate, whereafter the basic medium is passed over a base resin to separate impurities.

In light of this and other background in the area, there remains a need for improved, effective processes for purifying and recovering carboxylic acids and other valuable products. The present invention addresses these needs.

SUMMARY OF THE INVENTION

Accordingly, one preferred embodiment of the invention provides a process for separating an acid from one or more impurities, which involves thermally-managed chromatographic separation and elution phases. Thus, provided is a preferred process for the recovery of an acid from its mixture with an impurity, which includes a chromatographic separation of the acid from the impurity over an adsorbent resin at a first temperature, followed by elution of the acid product from the adsorbent resin at a second temperature higher, e.g. at least 10° C. higher, than the first temperature. More preferred processes employ a contacting zone containing an adsorbent which exhibits higher affinity for the acid than the one or more impurities, and increasing affinity for the acid with decreasing temperature. A first solution containing the acid and the impurity is introduced into the contacting zone. In order to establish high operating capacity, the solution can contain the acid at a level which substantially exceeds the capacity of the adsorbent to adsorb the acid. A second solution (eluent) is passed through the contacting zone. This second solution is passed at a first temperature and under conditions which are effective to establish a front of acid separated in the contacting zone from a front of the one or more impurities. The front of acid is then eluted from the contacting zone with a liquid at a second temperature higher, e.g. at least 10° C. or 20° C. higher, than the. first temperature. In this manner, during the separation phase, the affinity of the adsorbent for the acid is maintained at a relatively high level, which retards the acid and facilitates separation of the acid from the one or more impurities, whereas during the elution phase, the affinity of the adsorbent for the acid is maintained at a relatively low level, resulting in increased amounts of eluted acid over a given period of time. Thus, preferred processes of the invention can utilize traditional adsorption/thermal desorption phenomena in a chromatographic separation to achieve effective purification of an acid product from one or more impurities, and recovery of highly concentrated product fractions.

Particularly preferred inventive processes employ a continuous contacting apparatus including a plurality of resin-filled contacting zones (e.g. resin columns). A chromatographic separation zone is established including a plurality of the contacting zones together containing a sufficient amount of adsorbent to achieve substantial separation of the acid from the impurity. The chromatographic separation zone is operated at a first, relatively low temperature. An elution zone is established, from which the product acid is eluted once substantially separated from the impurity. The elution zone is operated at a second temperature which is higher than the first temperature. After the elution zone, resin-filled contacting zones (now substantially devoid of product) are preferably subjected to a cooling step so as to obtain optimum temperatures for the separation zone in the next cycle in the continuous contacting apparatus. The preferred cooling step includes passing a liquid medium at a temperature lower than the resin through the contacting zone. Continuous contacting apparatuses can be appropriately valved to sequentially subject the contacting zones to separation, heating, elution and cooling steps and carry out thermally-managed chromatographic separation processes of the invention.

In accordance with another aspect of the invention, a thermally-managed chromatographic separation process includes establishing a process wherein a plurality of contacting zones containing adsorbent are sequentially processed, the processing including passing over the adsorbent a liquid medium containing the product at a level exceeding the capacity of the adsorbent for the product, causing the chromatographic separation of the acid product from the impurity at a first temperature, and then eluting the product at a second temperature at least 10° C. higher than the first temperature. In this and other aspects of the invention, a portion of a product-containing medium from a prior-processed contacting zone can be included in the eluent used in the chromatographic separation phase.

Another preferred embodiment of the invention provides a process for the dewatering and recovery of an organic acid product from an aqueous solution, which includes chromatographically treating the aqueous solution of acid product over an adsorbent resin using a water-miscible solvent such as an alcohol as a mobile phase, under conditions wherein the acid product is eluted in an alcohol solution substantially free from water. Such a process is advantageously performed by providing a contacting zone containing an adsorbent which exhibits higher affinity for the acid than for water, and introducing an aqueous solution of the acid into the contacting zone. A liquid alcohol is passed through the contacting zone under conditions which are effective to establish a front of the organic acid separated in the contacting zone from a front of the water, and the front of organic acid is eluted from the contacting zone so as to provide an eluate containing the organic acid in solution in the alcohol, wherein the eluate being substantially free from water (i.e. contains no more than about 15% by weight water).

Still another preferred chromatographic process for dewatering an organic acid product includes the steps of:

(a) providing a plurality of contacting zones containing an adsorbent which exhibits higher affinity for the acid product than for water;

(b) sequentially processing the contacting zones through a chromatographic separation zone wherein an alcohol eluent solution and an aqueous solution containing the acid are together passed through the contacting zones to achieve a chromatographic process in which the acid is separated from the water; and (c) after step (b), sequentially processing the contacting zones through an elution zone so as to elute the acid product from the one or more contacting zones in a solution of the alcohol which is substantially free from water.

Thermally-managed inventive processes provide for the recovery of products in concentrated liquid mediums while efficiently utilizing thermal energy to aid in the recovery, and also while operating in configurations which provide high capacity and reduce adsorbent inventory requirements. Dewatering processes of the invention provide the recovery of acids in an eluate substantially free from water, thus facilitating recovery of the acid and/or facilitating reactions of the acid to be conducted in a subsequent operation. The invention also provides processes which are easy to operate, and which can be employed to recover a wide variety of desired product products in concentrated solutions. Additional preferred embodiments, features and advantages of the invention will be apparent from the following description.

DESCRIPTION OF THE PREFERRED EMBODIMENTS

Figure 1A:
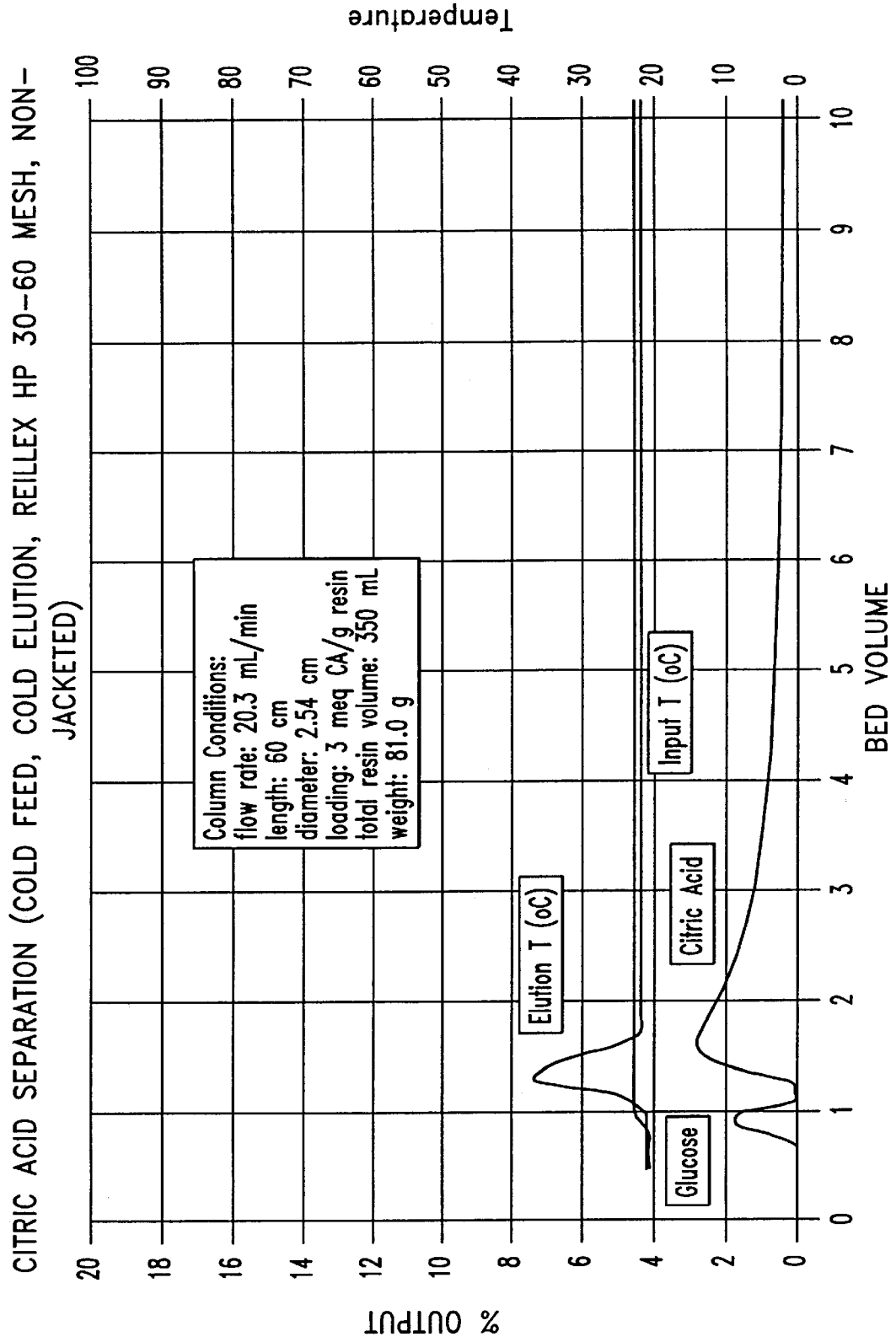
FIGS. 1A and 1B are graphs showing elution profiles for aqueous citric acid/glucose mixtures chromatographically treated over REILLEX™HP crosslinked polyvinylpyridine polymer under cold feed/elution (FIG. 1A) and hot feed/elution (FIG. 1B) conditions.

For the purposes of promoting an understanding of the principles of the invention, reference will now be made to certain of its embodiments and specific language will be used to describe the same. It will nevertheless be understood that no limitation of the scope of the invention is thereby intended, such alterations and modifications and applications of the principles of the invention as described herein being contemplated as would normally occur to one skilled in the art to which the invention pertains.

As indicated above, one preferred embodiment of the present invention provides a thermally-managed chromatographic separation process for the separation of a product from an impurity over an adsorbent resin, and recovery of the product. Featured processes of the invention use adsorbent resins and phenomena traditionally associated with adsorption/thermal desorption operations in chromatographic separations. Thus, to separate an acid product from one or more impurities in solution, a contacting zone is employed which contains an adsorbent which exhibits higher affinity for the acid than the one or more impurities, and increasing affinity for the acid with decreasing temperature. A first solution containing the acid and the impurity is introduced into the contacting zone. In order to establish high operating capacity and more effectively utilize the adsorbent for chromatographic-type separation, the solution preferably contains the acid in high concentration, for example optionally at a level which substantially exceeds the capacity of the adsorbent to adsorb the acid. After introduction of the acid/impurity containing solution, a second liquid, for example water, an aqueous solution containing the acid but which is essentially free from the impurity, or an organic solvent, is passed through the contacting zone at a first temperature and under conditions which are effective to establish a front of the acid separated in the contacting zone from a front of the one or more impurities. The front of acid is then eluted from the contacting zone with a liquid medium at a second temperature higher than the first temperature, for example 10° C. and more preferably at least 20° C. higher than the first temperature. In this manner, a chromatographic process is established which is "thermally-managed" in that during the separation phase the affinity of the adsorbent for the acid is maintained at a relatively high level—facilitating separation of the acid and one or more impurities—and during the elution phase, after the impurities have been separated from the acid front, the affinity of the adsorbent for the acid is maintained at a relatively low level—facilitating removal or elution of the acid from the contacting zone and results in increased amounts of eluted acid over a given period of time. Thus, such preferred processes of the invention can capitalize upon traditional adsorption/thermal desorption phenomena in a chromatographic separation to achieve effective purification of an acid product from one or more impurities, and recovery of highly concentrated product fractions.

In general, liquid-solid separation processes for recovering valuable chemical products are known, and a wide variety of adsorbent resins and appropriate liquid eluents have been identified. Thus, those ordinarily skilled in the art will be readily able to select and use suitable adsorbent resins and eluent mediums in accordance with the present invention.

Generally speaking, the adsorbent employed will have the capacity adsorb the desired product, and will be stable (i.e. will not undergo substantial degradation) under the processing conditions utilized as further described below. Although the adsorbent can be any substance capable of adsorbing the desired product (including activated carbon, zeolites, etc.), more desirable adsorbents for use in the invention will be polymeric adsorbent resins which are crosslinked to provide thermal and mechanical stability and an advantageous physical form. Bead-form adsorbent resins are preferred, especially those having a particle size of about 20 to about 200 mesh, more especially about 40 to about 120 mesh.

A wide variety of suitable polymeric adsorbents have been reported for the recovery of desired adsorbate products such as carboxylic or other acids, and can be used as a stationary phase in thermally-managed chromatographic recovery processes of the invention. These polymeric adsorbents are formed through the polymerization of one or more monomers usually including a crosslinking monomer. The polymerization is carried out to provide resin beads in either gel or macroreticular form. Further, these resin beads can be chemically modified, e.g. by adding ionic groups to the resin such as quaternary salt or acid salt groups. The resulting resin can thus be anionic, cationic or nonionic and have a variety of physical and chemical characteristics.

For example, suitable reported resins include nonionic and ionic polymers, including neutral, noniogenic, macroreticular, water-insoluble cross-linked styrene-poly(vinyl)benzene, basic polymer materials such as cross-linked pyridine-containing polymers, e.g. vinylpyridine polymers, cross-linked acrylic or styrene resin matrices having attached tertiary amine functional groups or pyridine functional groups, cross-linked acrylic or styrene resin matrices having attached aliphatic quaternary amine functional groups, and the like (see e.g. Kawabata and Kulprathipanja et al. patents cited in the Background). These and numerous other polymers known in the art for use as adsorbents, for example base or acid ion exchange resins including styrenic, acrylic, epoxy amine, styrene polyamine, and phenol formaldehyde, or nonionic adsorption resins, will be suitable for use in temperature swing adsorption/desorption processes in accordance with the invention; preferably, however, the polymer adsorbent will be a crosslinked base polymer, such as a crosslinked polymer containing N-aliphatic or N-heterocyclic tertiary amine functions, for example polymers containing dialkylamino or pyridine functionalities.

Particularly preferred pyridine-containing polymers are polyvinylpyridine polymers such as poly 2- and poly 4-vinylpyridine gel or macroreticular resins exhibiting a bead form. These resins are preferably at least about 2% cross-linked with a suitable cross-linking agent, such as divinylbenzene. More preferred resins are 2 to 50% crosslinked bead-form vinylpyridine polymers, e.g. poly 2- and poly 4-vinylpyridine polymers.

For example, more preferred resins include poly 2- and poly 4-vinylpyridine resins available from Reilly Industries, Inc., Indianapolis, Ind., in the REILLEX™ polymer series. These REILLEX™ polymers are generally 2% or more crosslinked, and exhibit good thermal stability and adsorptive and desorptive capacities and other preferred features as described herein. For example, preferred resins of this type have exhibited desorptive capacities of at least about 200 mg citric acid per gram of polymer. Additional preferred resins are available from this same source under the REILLEX™HP polymer series. These REILLEX™HP polymers also exhibit advantageous capacities, and are highly regenerable. For more information about these REILLEX™ polymers, reference can be made to the literature, including that available from Reilly Industries, Inc. in the form of REILLEX™ reports 1, 2 and 3.

Other resins, for example AMBERLYST A-21, AMBERLITE IRA 68, or AMBERLITE IRA 93 resins from Rohm and Haas, Philadelphia, Pa., or DOWEX MWA-1 resin from Dow Chemical, can also be used in the invention. Among these resins, the A-21 resin is crosslinked by divinylbenzene (greater than 2%) and contains aliphatic tertiary amine functions (particularly, attached dialkylamino (dimethylamino) groups); the IRA 68 resin contains aliphatic tertiary amine groups, a divinylbenzene-crosslinked acrylic matrix, and exhibits a gel form; and the IRA 93 and MWA-1 resins contain aliphatic tertiary amine groups, and are based on a divinylbenzene-crosslinked styrene matrix, exhibiting a macroreticular form. For additional information about these and other similar resins which can be used in the invention, reference can be made to the literature including that available from the manufacturers.

Thermally-managed processes of the invention will provide particular advantage where the equilibrium concentration between the product of interest and the adsorbent changes significantly with changes in temperature, e.g. such that the adsorbent has a substantially greater capacity (i.e. at least 5% greater on a milliequivalents per gram of dry adsorbent basis) to adsorb or retard the desired acid product at relatively low temperatures as compared to higher temperatures. Acids are preferred products to be recovered in accordance with the invention, particularly acids having pKa's in the range of about 2.0 to about 4.5. More generally, suitable acids will have pK's in the range of about 2.0 to about 6.0, with one preferred group having pKa's of about 3.0 to about 5.0. Illustrative acids for use in the invention include, for example, aromatic acids such as phenol, salicylic acid, ortho-phthalic acid, meta-phthalic acid, benzoic acid, 3-chlorobenzoic acid; alpha-hydroxy acids such as citric acid, lactic acid, dilactic acid, malic acid, mandelic acid, benzilic acid, glyoxylic acid, glycolic acid, tartaric acid, formic acid, glutaric acid, fumaric acid, acetylacetic acid, acetic acid, succinic acid, itaconic acid; pyridinecarboxylic acids such as nicotinic acid or isonicotinic acid; piperidinecarboxylic acids such as isonipecotic acid; inorganic acids such as sulfonic acid, tungstic acid, molybdic acid, gallium (III) ion, mercury (II) ion, and the like. For additional acids suitable for use in the present invention, reference can be made to the acids identified in U.S. Pat. Nos. 4,552,905, 4,323,702 and 5,412,126. Of particular interest in the invention is the recovery of organic acids, especially carboxylic acids such as aliphatic carboxylic acids, from mediums in which they have been produced by fermentation, i.e. by the fermentation of suitable carbon sources by microorganisms.

For example, substantial worldwide production of organic carboxylic acids such as citric and lactic acids is performed by fermentation. In the case of citric acid, the broth may be from a fermentation of a carbon source such as corn sugar or molasses with a suitable citric-acid-producing bacteria or other microorganism such as *Aspergillus Niger*. Lactic acid is produced using bacteria or other microorganisms capable of forming lactic acid upon metabolizing a carbon source. Typically, bacteria of the Family Lactobacillaceae are employed, although other microorganisms such as fungi may be used. For example, fungi of the family Rhizopus, such as *Rhizopus oryzae* NRRL 395 (United States Department of Agriculture, Peoria, Ill.), can be employed to produce substantially pure L+ lactic acid as generally taught in International Application No. PCT/US92/07738 filed Sep. 14, 1992 by Reilly Industries, Inc. (published Apr. 1, 1993, WO 93106226). It is well within the purview of the skilled artisan to select and use suitable fermentation organisms to produce fermentation broths containing organic acids such as carboxylic acids, which broths can be treated in accordance with the invention to recover the acids.

When a carboxylic acid-containing fermentation medium is involved, it will usually contain water, the product acid, salts, amino acids, sugars, and other various components in minor amounts. Such fermentation mediums can be filtered to remove suspended solids prior to the adsorption step. In addition, in accordance with the present invention, the carboxylic acid-containing fermentation medium can be taken from an ongoing fermentation producing the carboxylic acid, and the removal of the acid can thereby be coupled to its fermentive production, for example as described for lactic acid in WO 93/06226 published Apr. 1 1993 (publishing International Application No. PCT/US92/07738, filed Sep. 14 1992). In such coupled processes, the feed into the separation process can be a portion of the fermentation medium, desirably after filtration or other treatments suitable for preparing the feed for passage into separation processes of the invention. The carboxylic acid is recovered by a separation process as described herein, and a carboxylic acid-depleted "waste" effluent stream from the separation process can be returned to the fermenter, thus returning nutrients for the fermentation. Such processes can effectively reduce feedback inhibition of the acid-producing cells by the acid product, for example as is known to occur in lactic acid fermentations.

A variety of liquid eluents can be employed in the present invention. These eluents include, for example, organic solvents, e.g. aromatic solvents or polar organic solvents such as alcohols (e.g. $C_1$–$C_5$ alcohols such as methanol, ethanol, propanol, isopropanol, butanol and methylisobutyl carbinol), ketones and esters, as well as aqueous mediums such as water (i.e. substantially pure water without added solutes), aqueous solutions of acids or bases, e.g. hydrochloric acid, sulfuric acid or sodium hydroxide solutions, or water/organic co-solvent mediums such as water/alcohol mixtures. Some preferred inventive processes employ water so as to provide desorbate mediums free from unnecessary solutes or co-solvents which may complicate recovery of the desired product. Other preferred inventive processes employ organic solvents such as alcohols in a fashion so as to dewater the acid product and recover the acid product in an organic solvent. When alcohols are used in such processes, the product can be recovered in alcohol with a minimal amount (e.g. less than 20% by weight, preferably less than 10% by weight) of water, and for example in the case of carboxylic acids (e.g. citric acid), the recovered product medium can be reacted in an esterification process to provide a corresponding carboxylic acid ester or partial ester.

Generally, the elution phases of thermally-managed processes of the invention will involve the use of elevated temperatures relative to the separation phase, those temperatures being sufficient to effectively elute the product from the adsorbent resin. The particular elution temperature used will depend on several factors such as the acid product of interest, the eluent used, etc. Temperatures up to the boiling point, or exceeding the boiling point of the eluent (e.g. at superatmospheric pressure) will be suitable. In preferred processes, the elution temperature will generally be above about 50° C., more typically above about 70° C. and often above about 90° C. When recovering carboxylic acids such as citric or lactic acid, desorption temperatures above about 90° C. will be preferred.

In preferred thermally-managed chromatographic processes of the invention, concentrated product feeds containing the product at high levels, In some processes, product levels which substantially exceed the capacity of the adsorbent may be used, e.g. exceeding such capacity by 20% or more, or even 100% or more, such that when the feed is passed into the columns, a separation zone is established wherein there is more product in the separation zone than the adsorbent in the separation zone can adsorb. In this regard, the capacity of the adsorbent to adsorb a product of interest is a well known expression, and can be determined, for example, by computing the difference in product adsorbed by the adsorbent in contact with product in solution at constant concentration as shown in equilibrium isotherm diagrams. It will be understood that the particular product feed concentration employed will be selected based upon various factors at hand, including for example the desire to maximize the use of the resin while at the same time achieving product streams of the requisite purity.

Using such concentrated feeds, one utilizes the resin more efficiently for separation, and achieves operating capacities significantly higher than those encountered which using product loadings at or below the adsorption capacity of the adsorbent. For example, in the specific Examples given below, in a process conducted and described in conjunction with FIG. 12, a 50% citric acid feed was used (exceeding the capacity of the resin by more than 200%), and resulted in a process which achieved an operating capacity in excess of 3 milliquivalents of citric acid per gram of adsorbent (dry). Such high levels of adsorbent utilization decrease adsorbent inventory requirements and increase throughput. These are significant advantages which can be capitalized upon in large scale separation processes.

Thus, in more preferred processes for separating citric acid from impurities such as sugars, a concentrated solution of citric acid, for example having a concentration exceeding about 25%, more preferably exceeding 30%, is used as the product feed. The concentrated feed of citric acid can be obtained, for example, by concentrating a citric acid-containing aqueous medium from a fermentation initially having a citric acid level of less than about 20%. This concentrating step can be accomplished in any acceptable fashion, for instance including evaporation of water from the medium. The thus concentrated medium, having an increased citric acid concentration, is then used as feed into the inventive processes.

In another feature of the invention, it has been discovered that relatively weak acids, for example weak carboxylic acids having pKa's above 3.5, e.g. 3.5 to 6.0, such as lactic acid or acetic acid, can be effectively dewatered while achieving advantageous elution profiles under isothermal chromatographic conditions, as well as under the thermally-managed conditions as discussed above. Thus, as illustrated in Example 13 below, an aqueous solution of the weak acid can be added to a chromatic separation zone through which is passed a polar organic solvent such as an alcohol as the eluent. The adsorbent in the separation zone, preferably containing tertiary amino groups such as pyridinyl groups, exhibits a higher affinity for the acid than for the water, and a separation is achieved such that an eluent is obtained containing the acid in an alcohol solution substantially free from water. In this regard, as used in this context, "substantially free from" is intended to mean that the alcohol solution containing the recovered acid product contains at most about 20% by weight of water. More preferably, the recovered alcohol solution contains no more than about 10% by weight, and most preferably no more than about 5% by weight. Moreover, in preferred processes, the recovered alcohol solution will contain the acid product in high concentration relative to the input concentration. For instance, in preferred processes the acid concentration in the recovered alcohol eluent will be at least about 50% of that in the aqueous acid feed, more preferably at least about 75%.

More preferred thermally managed and dewatering processes of the invention will involve the feed of an eluent medium containing the product to the separation phase of the process. Such product-containing eluents, for example resultant of a prior elution operation to recover the product, can be used to effectively assist in the separation of the impurity from the acid product and, at the same time, the presence of product in the eluent will increase the concentration of the product in the final product stream. Thus, in preferred operations a portion of the product eluent stream from a continuous recovery operation is diverted to the rinse step in order to provide an increase in concentration of the product in the product stream.

Favored processes of the invention are conducted using a continuous contacting apparatus ("CCA"). For example, continuous contacting apparatuses which are useful in the invention include those such as the ISEP or CSEP Continuous Contactors available from Advanced Separations Technology, Inc. (AST, Inc.), Lakeland, Florida, and are also generally described in U.S. Pat. No. 4,764,276 issued Aug. 16, 1988, U.S. Pat. No. 4,808,317 issued Feb. 28, 1989 and U.S. Pat. No. 4,522,726 issued Jun. 11, 1985. A brief description of such a CCA device as described in these patents is set forth below. For further details as to the design and operation of CCA's suitable for use in the invention, reference can be made to literature available from AST, Inc. including "The ISEP™ Principle Of Continuous Adsorption", and as well to the above-cited U.S. patents.

The preferred CCA for use in the present invention will be a liquid-solid contact apparatus including a plurality of chambers which are adapted to receive solid adsorbent material and which taken together or separately may provide a contacting zone for processes of the invention. The chambers have respective inlet and outlet ports, and are mounted for rotation about a central axis so as to advance the chambers past supply and discharge ports which cooperate with the inlet and outlet ports. In particular, liquid is supplied individually to inlet ports at the top of these chambers through conduits connected with a valve assembly above the chambers, which valve assembly provides a plurality of supply ports which cooperate with inlet ports of the chambers as they are advanced. Similarly, conduits connect the outlet port at the lower end of each chamber with a valve assembly below the chambers which provides discharge ports which cooperate with the outlet ports as the chambers are advanced. The valve assemblies include movable plates with slots that cover and uncover inlet ports as the plate rotates with the carousel. By varying the size of the slots in the plate and the location of the slots, the flow from the supply conduits into the chamber and flow from the chamber to the exhaust conduits can be controlled in a predetermined manner. The motion of one plate over the other can be continuous or as an indexed motion. The time during which liquid flows into and out of the chambers is a function of the speed of rotation of the chambers about the central axis.

Figure 10:
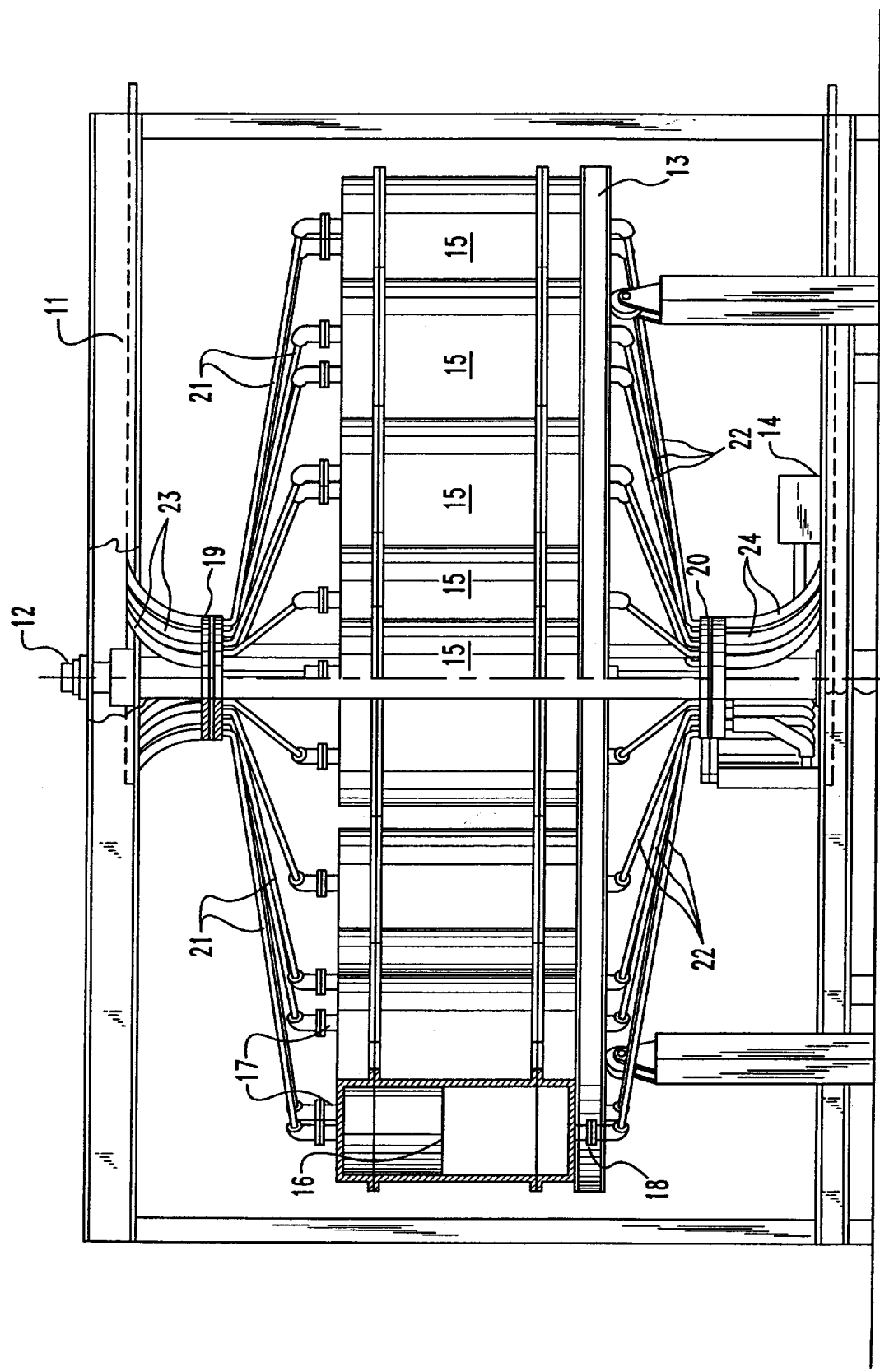
FIG. 10 is a side elevational view partially in cross-section of an illustrative continuous contacting apparatus which can be used in the present invention.

More specifically, a preferred contacting device for use in the invention is shown generally in FIG. 10. The apparatus includes a rectangular frame 11 which supports a vertical drive shaft 12. A carousel 13 is mounted for rotation on the drive shaft. The carousel is fixed to the shaft and the shaft is driven by a motor 14 mounted on the frame 11. A plurality of cylindrical chambers 15 (e.g. 30 chambers) are mounted vertically on the carousel 13. The chambers are preferably arranged in staggered relation around the circumference of the carousel. Each of the chambers is filled with resin or other suitable solid adsorbent material according to the particular process being performed. As shown at the left side of FIG. 10 in cross-section, the solid adsorbent material 16 is preferably filled to about one-half or more of the height of the chamber 15. An arrangement is provided on each chamber 15 for inserting and removing the solid material through the top of the container. Pipe fittings 17 and 18 are provided at inlet and outlet openings on the top and bottom, respectively, of each chamber 15. An upper valve body 19 and a lower valve body 20 are mounted over the drive shaft 12. The valve bodies 19 and 20 provide supply and discharge ports, respectively (e.g. 20 each). Individual conduits 21 and 22 connect the valve bodies 19 and 20 with the respective upper and lower pipe fittings 17 and 18, so as to allow cooperation of the supply and discharge ports. of valve bodies 19 and 20 with the inlet and outlet ports of the chambers 15. Supply conduits 23 (discharge is also possible) are mounted in the top of the. frame 11 and extend upwardly from the valve body 19. Similarly, discharge conduits 24 (supply is also possible) extend downwardly from the lower valve body 19 to the frame 11. In this manner, as the carousel is rotated to advance the chambers 15, the inlet and outlet ports of the chambers 15 cooperate with the supply and discharge ports of the valve bodies 19 and 20 to provide advantageous means for circulating liquids through the chambers 15.

In accordance with one aspect of the invention, the apparatus of FIG. 10 will preferably be configured so as to include separation and elution zones. The separation zone can be conventionally operated so as to separate the material of interest, e.g. citric acid, from the impurity over an adsorbent resin contained within chambers 15 from a feed solution. Generally, a feed solution containing the citric acid or other product will be passed countercurrent through the chambers 15 and over the resin. It will be understood that the number of ports of the CCA dedicated to the separation and elution zones may vary, and will be determined so as to maximize overall process economics. In addition, it will be understood that the advantageous use of product stream in the separation zone as discussed above can be achieved by diverting a portion of the product from the elution zone to the separation zone. Specific illustrations of such configurations are discussed below in connection with the FIGS. 11 and 12.

EXAMPLES 1–9

General Procedure

For these Examples a series of pulse tests were conducted to demonstrate the applicability of thermally-managed chromatography to various acids and using differing tertiary amine-containing polymers. A column 60 cm in length and having a 2.54 cm inner was provided with separate feed lines for the eluent (water or alcohol) and the acid product feed. The column was either non-jacketed or jacketed with automatic temperature control, as indicated in the specific Example descriptions below. The eluent feed line included a heat exchanger to control the temperature of the eluent feed to the column, while the aqueous acid product/glucose mixture was fed at room temperature or heated, as indicated. Unless otherwise noted, the acid product was present at 50% by weight and the glucose at 2% by weight, a 100 g pulse of the product/glucose feed was provided to the column, and the loading on the column amounted to 3 meq acid per gram of resin, unless otherwise noted. As to column preparation, the column was loaded with a slurry of the appropriate resin and backwashed with water to remove air bubbles. Temperature controls were set and the system was brought to equilibrium by recirculating the eluent through the bed. The feed mixture was pumped onto the bed and immediately followed by the eluent. Samples eluting from the column were collected in volumetric increments, typically $\frac{1}{10}$ bed volume (BV) for the first three BV's, follow by ½ BV samples for the remainder of the collection period. Samples were analyzed using HPLC and appropriate standards. In each run, the resin volume was 350 mL.

Examples 1A and 1B

Figure 1B:
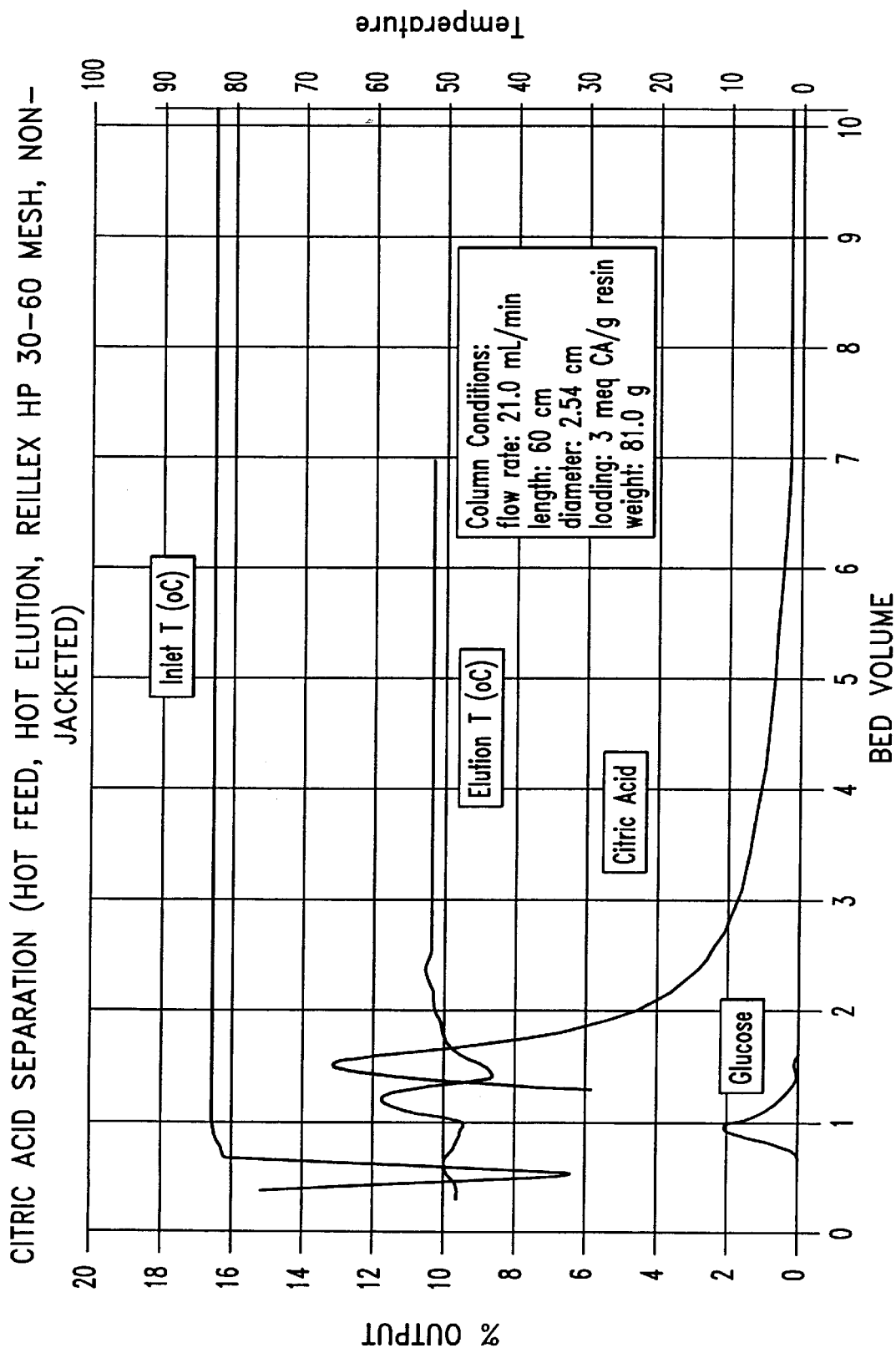

An aqueous citric acid/glucose product feed was treated over REILLEX™HP resin (30–60 mesh) at a flow rate of 20.3 mL/min in a non-jacketed column, using water as the eluent. For Example 1A, the feed and eluent temperatures were 25° C. For Example 1B, the feed and eluent temperatures were 75° C. and 86° C., respectively. The results are presented in respective FIGS. 1A and 1B. As shown in FIG. 1A, at relatively low temperatures a good separation of glucose and citric acid is achieved; however, the peak citric acid concentration reached only about 3% with substantial tailing occurring. On the other hand, as shown in FIG. 1B, at relatively high temperatures, the peak citric acid concentration is much higher but the separation from glucose is relatively poorer. Thus, the present invention is applicable with particular advantage to this separation, and using lower temperatures during the separation and higher temperatures applied to the migrating citric acid front after substantial separation has been achieved, both good separation and citric acid elution profiles can be obtained.

Example 2

Figure 2:
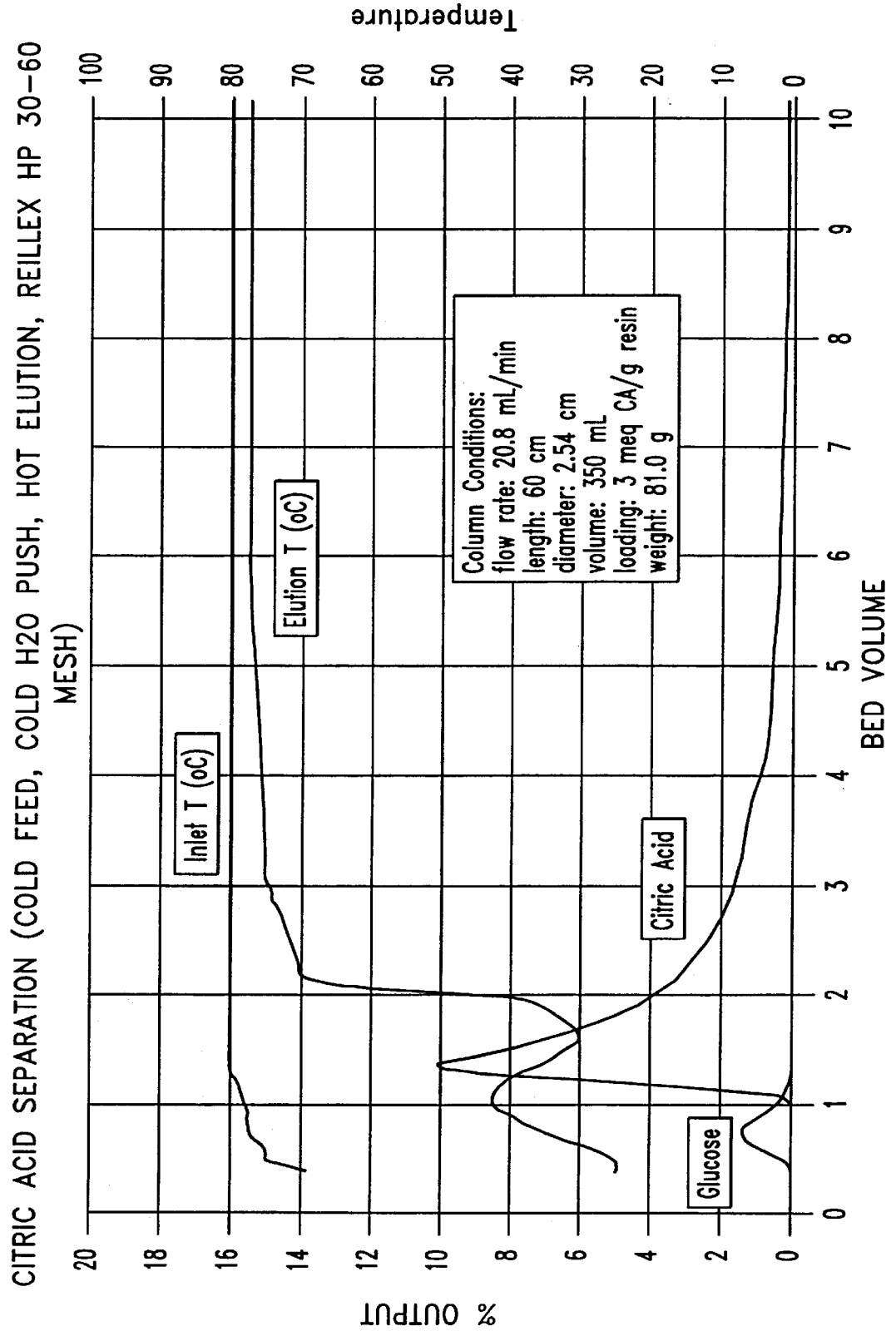
FIG. 2 is a graph showing the chromatographic elution profile for an aqueous citric acid/glucose mixture chromatographically treated over REILLEX™HP crosslinked polyvinylpyridine polymer under cold feed and hot elution conditions.

A citric acid/glucose product feed was treated over REILLEX™HP resin (30–60 mesh) at a flow rate of 20.8 mL/min in a non-jacketed column, using water as the eluent. The acid product feed temperature was 25° C., followed by a brief feed of water at 25° C. The eluent (water) was then fed at a temperature of 86° C. In this fashion, a relatively low temperature was maintained on the product/glucose front during its migration through the column in a separation phase, whereas a relatively high temperature occurred in the area of the citric acid front during elution. The specific results are presented in FIG. 2, which shows both an improved citric acid elution profile relative to FIG. 1A and an improved separation relative to FIG. 1B. Thus, thermal management of the column during separation and elution phases provides advantageous separation and product recovery.

Examples 3A and 3B

Figure 3A:
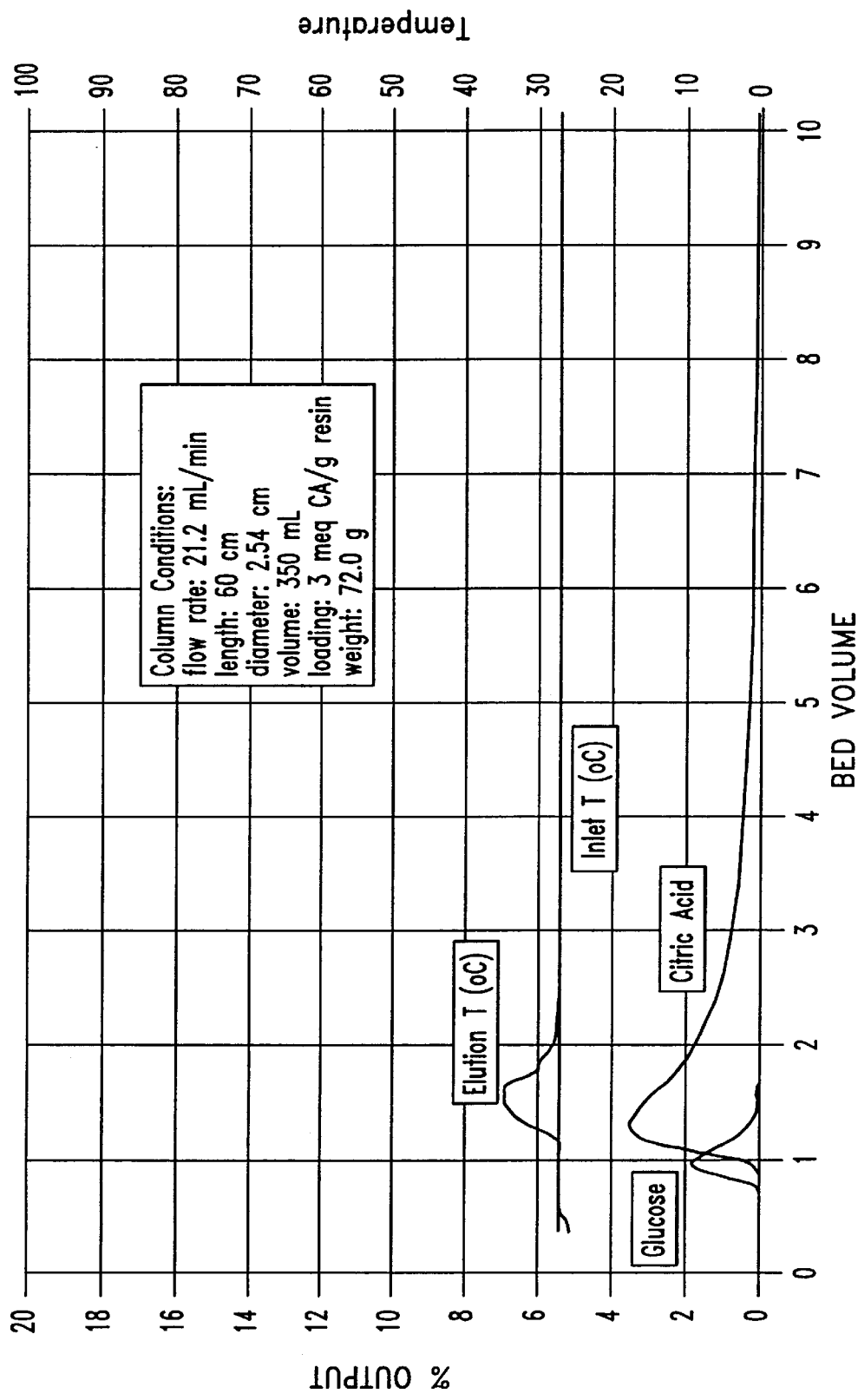
FIGS. 3A and 3B are graphs showing elution profiles for aqueous citric acid/glucose mixtures chromatographically treated over IRA-93 resin under cold feed/elution (3A) and hot feed/elution (3B) conditions.
Figure 3B:
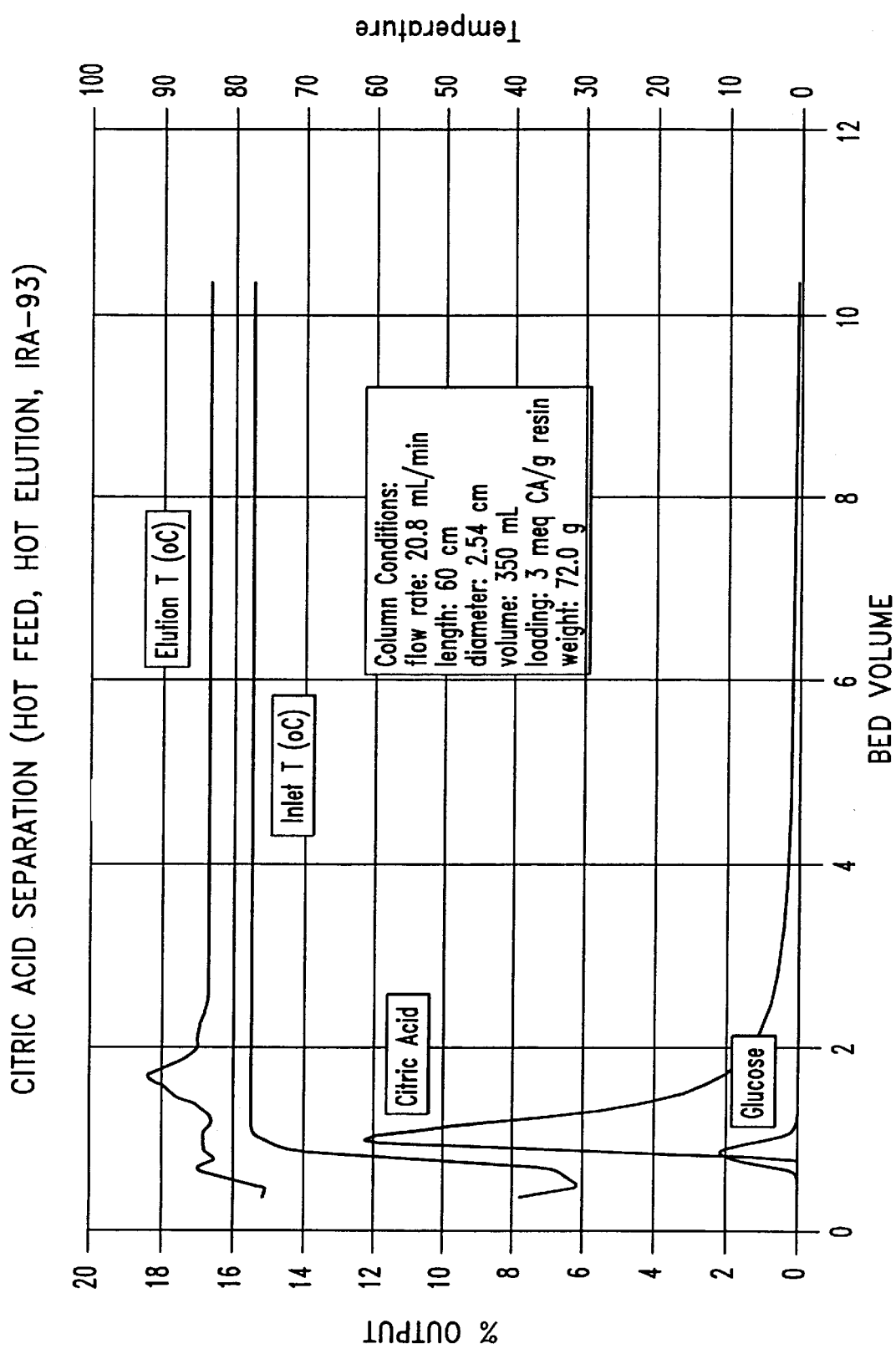

A citric acid/glucose product feed was treated over IRA-93 resin at a flow rate of about 21 mL/min in a jacketed column, using water as the eluent. For Example 3A, the feed and eluent temperatures were 25° C. For Example 3B, the feed and eluent temperatures were 85° C. and 86° C., respectively. The results are presented in respective FIGS. 3A and 3B. Generally as in FIGS. 1A and 1B. better separation occurs under low temperature feed/eluent conditions, while a more desirable elution profile of the citric acid occurs under higher temperature feed/eluent conditions. Again it is demonstrated that thermally-managed chromatography as in the present invention can be used to advantage in the separation.

Examples 4A and 4B

Figure 4A:
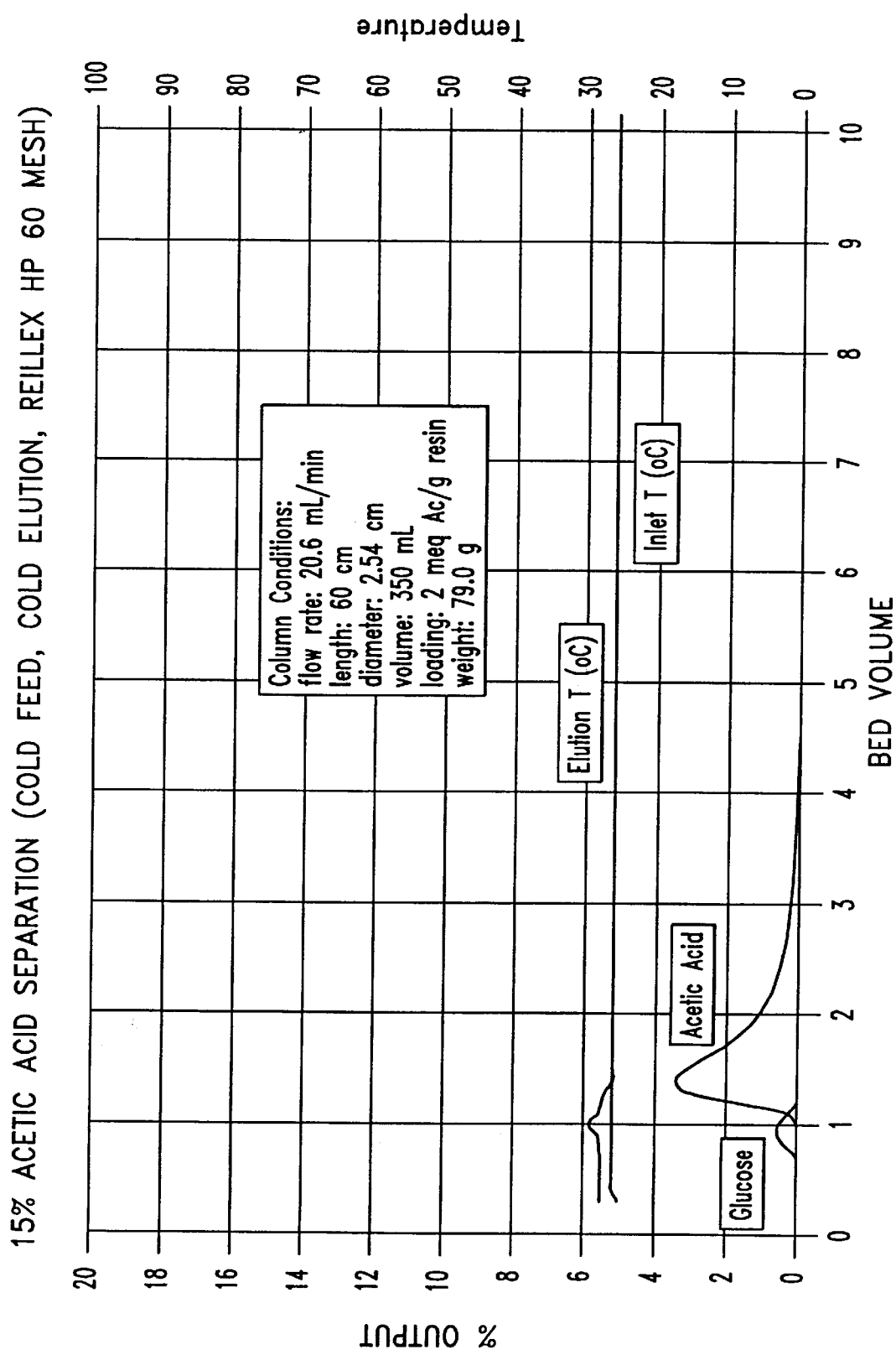
FIGS. 4A and 4B are graphs showing elution profiles for aqueous acetic acid/glucose mixtures chromatographically treated over REILLEX™HP crosslinked polyvinylpyridine polymer under cold feed/elution (4A) and hot feed/elution (4B) conditions.
Figure 4B:
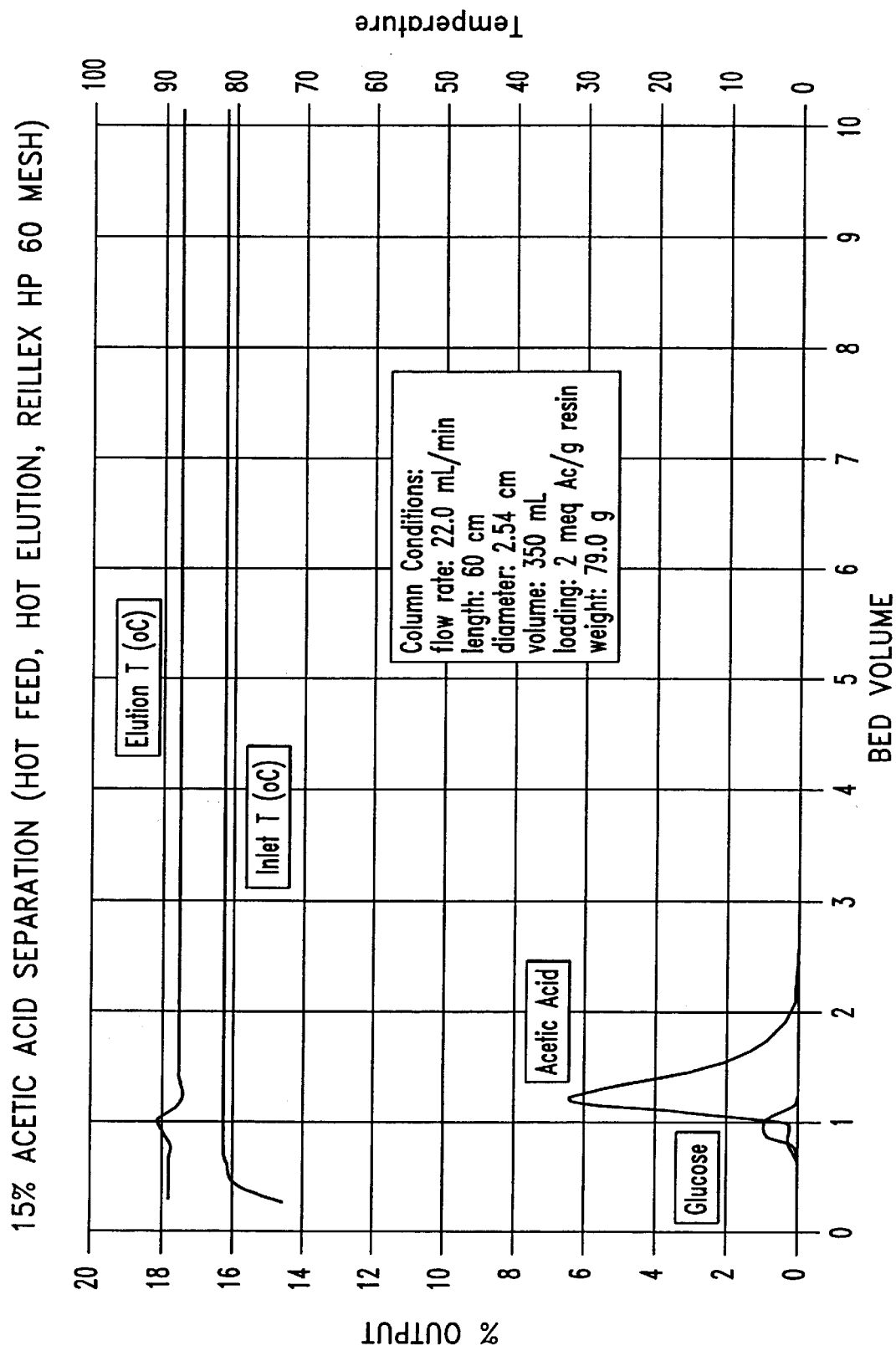

A 15%, acetic acid / 1% glucose product feed was treated over REILLEX™HP resin (30–60 mesh) in a jacketed column, using water as the eluent. 60.5 g of feed were put onto the column, and the loading on the resin was at a level of 2 meq acetic acid per gram of resin. For Example 4A, the flow rate was 20.6 mL/min and the feed and eluent temperatures were 25° C. For Example 4B, the flow rate was 22.0 mL/min and the feed and eluent temperatures were 85° C. and 86° C., respectively. The results are presented in respective FIGS. 4A and 4B, which show elution profiles illustrating the applicability of the present invention to the separation.

Examples 5A and 5B

Figure 5A:
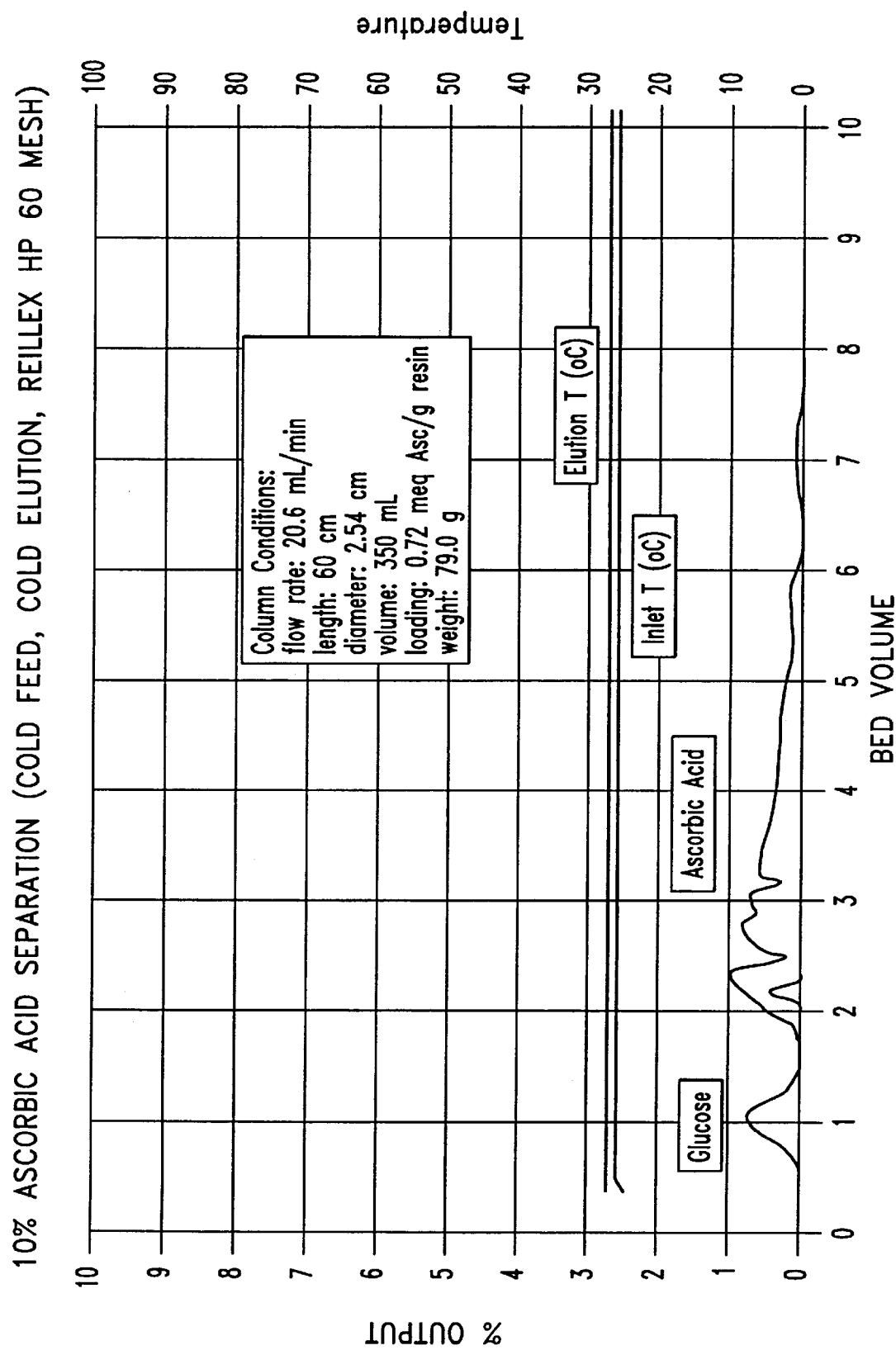
FIGS. 5A and 5B are graphs showing elution profiles for aqueous ascorbic acid/glucose mixtures chromatographically treated over REILLEX™HP crosslinked polyvinylpyridine polymer under cold feed/elution (5A) and hot feed/elution (5B) conditions.
Figure 5B:
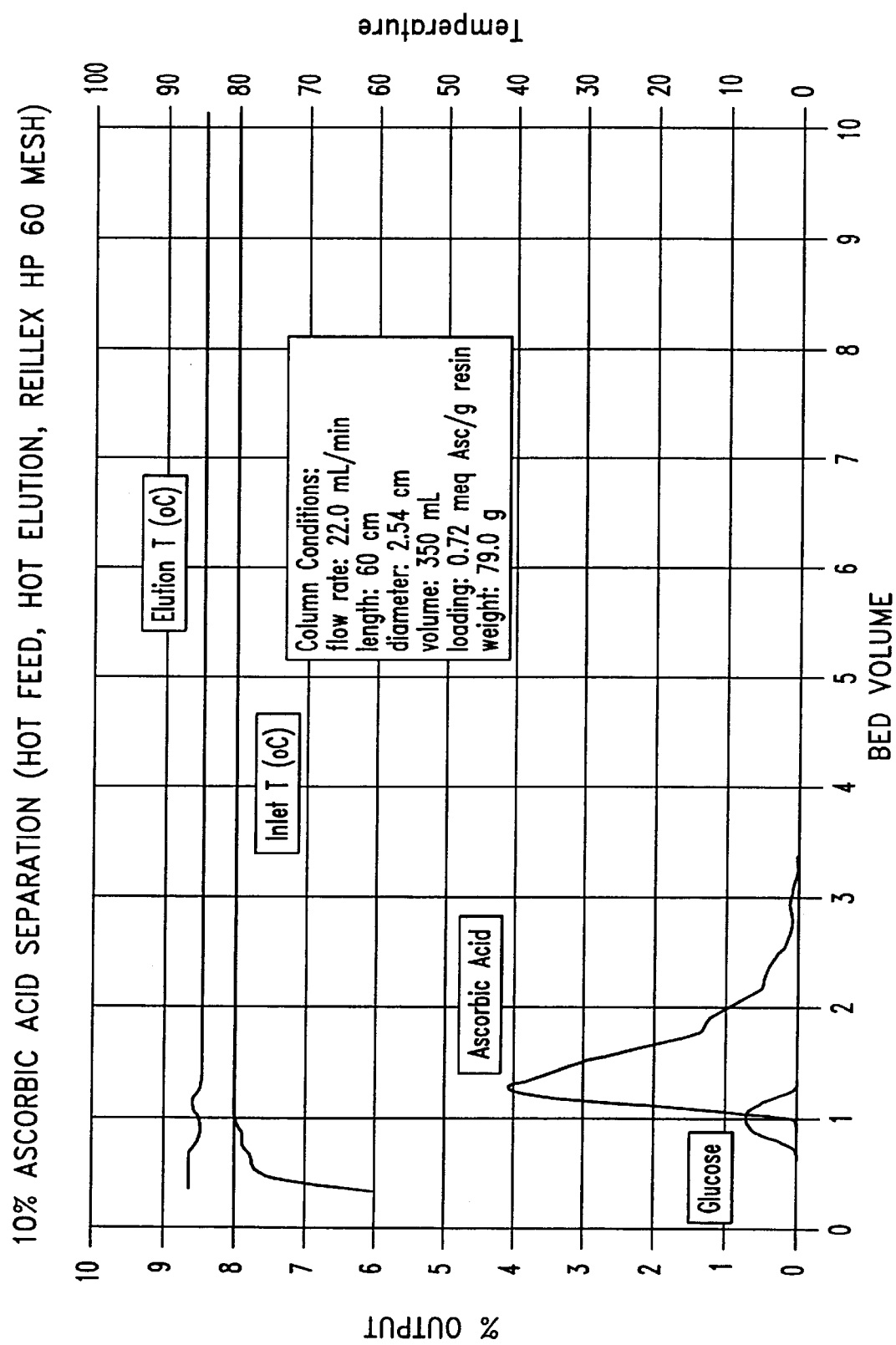

A 10%, ascorbic acid / 1% glucose product feed was treated over REILLEX™HP resin (30–60 mesh) in a jacketed column, using water as the eluent. A total of 205.5 g of feed was fed into the column, and the loading on the resin was 0.72 meq ascorbic acid per gram of resin. For Example 5A, the flow rate was 20.6 mL/min and the feed and eluent temperatures were 25° C. For Example 5B, the flow rate was 22.0 mL/min and the feed and eluent temperatures were 85° C. and 86° C., respectively. The results are presented in respective FIGS. 5A and 5B, similarly illustrating the applicability of the present invention to the separation and recovery of the ascorbic acid.

Examples 6A and 6B

Figure 6A:
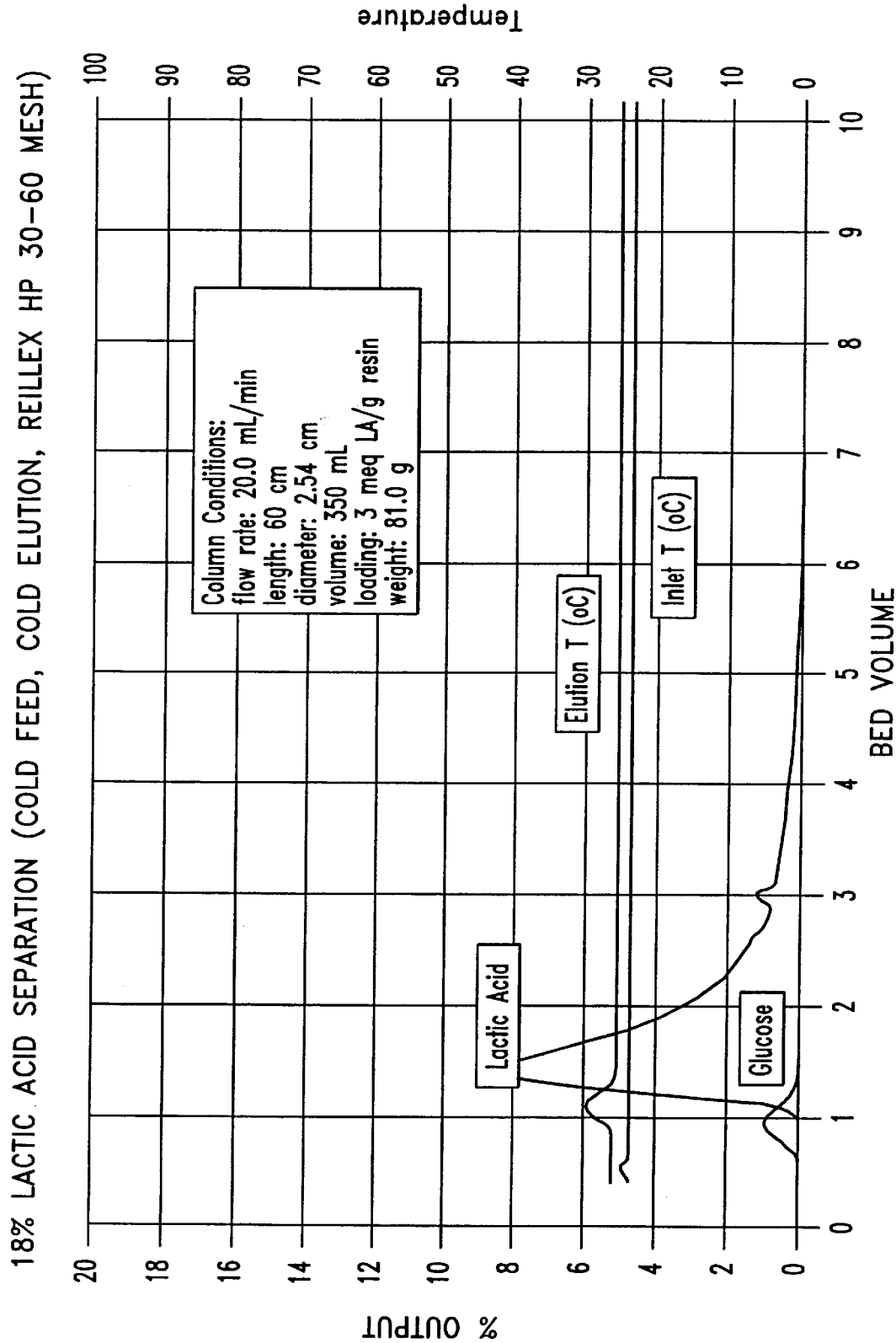
FIGS. 6A and 6B are graphs showing elution profiles for lactic acid/glucose mixtures chromatographically treated over REILLEX™HP crosslinked polyvinylpyridine polymer under cold feed/elution (6A) and hot feed/elution (6B) conditions.
Figure 6B:
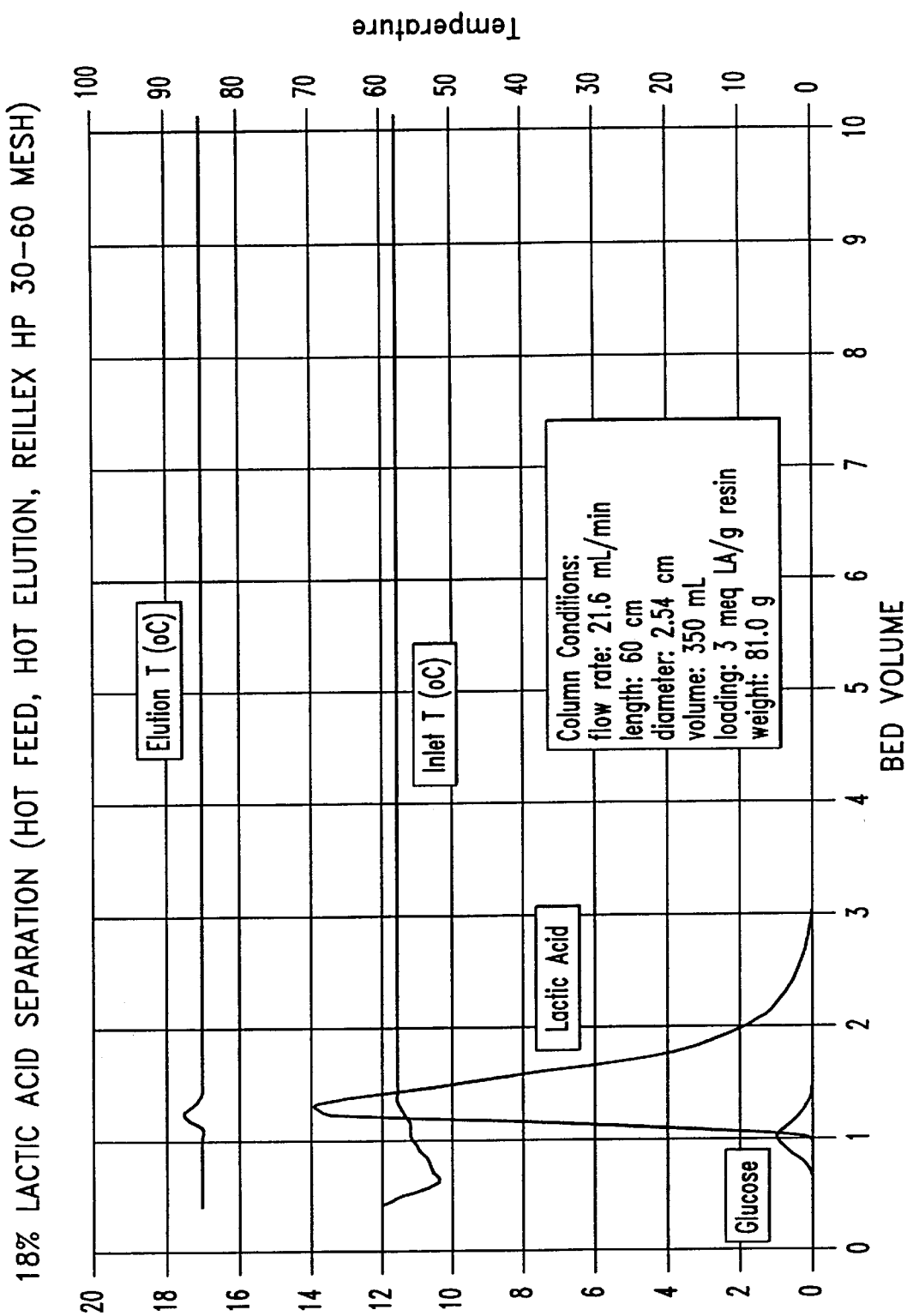

A 18%, lactic acid/1% glucose product feed was treated over REILLEX™HP resin (30–60 mesh) in a jacketed column, using water as the eluent. The loading on the resin was at a level of 3 meq lactic acid per gram of resin. For Example 6A, the flow rate was 20.0 mL/min and the feed and eluent temperatures were 25° C. For Example 6B, the flow rate was 21.6 mL/min and the feed and eluent temperatures were 85° C. and 86° C., respectively. The results as presented in FIGS. 6A and 6B show elution profiles illustrating the applicability of the present invention to the lactic acid separation.

Examples 7A and 7B

Figure 7A:
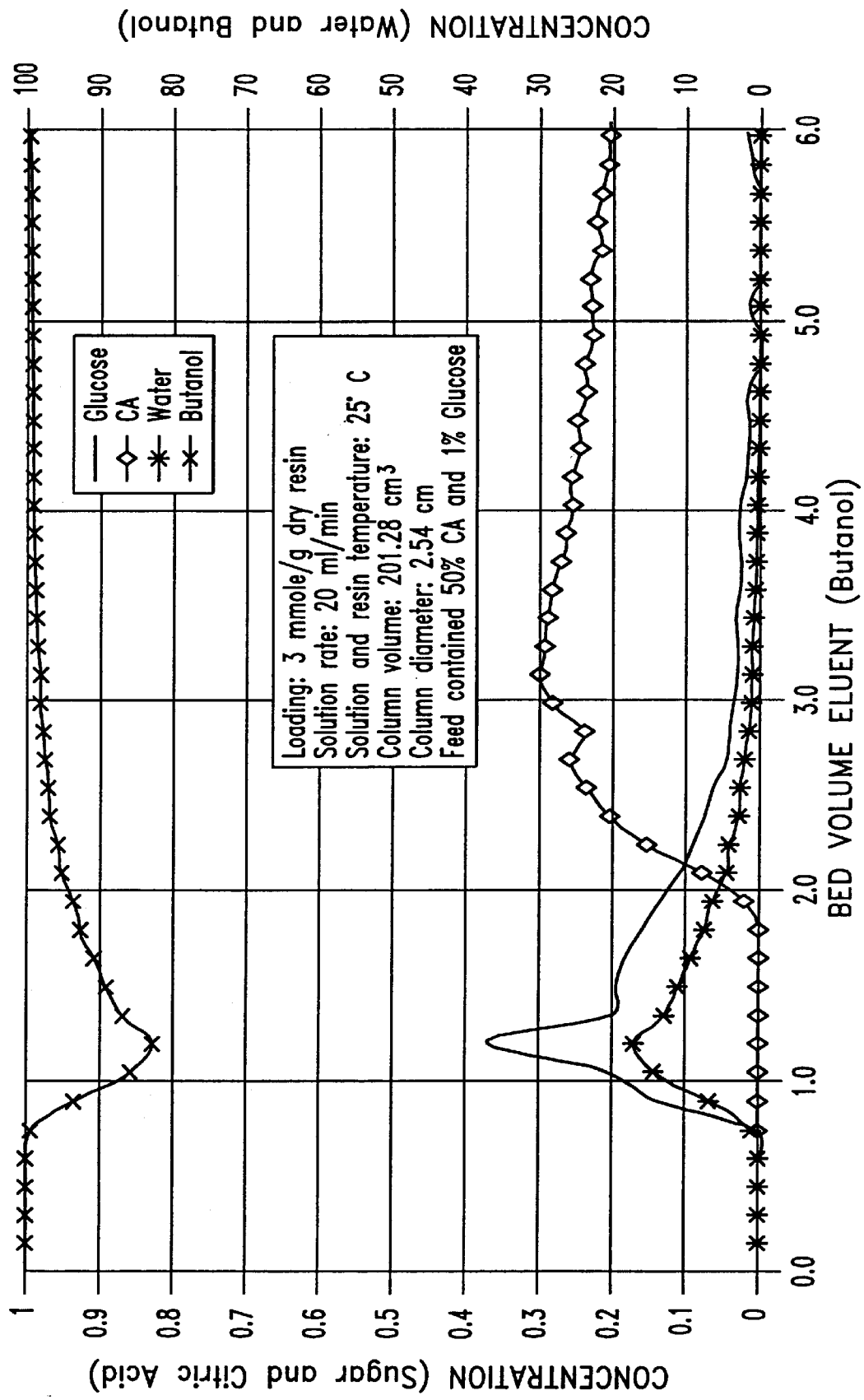
FIGS. 7A and 7b are graphs showing elution profiles for aqueous glucose/citric acid mixtures chromatographically treated over REILLEX™HP crosslinked polyvinylpyridine polymer using butanol as the eluent under cold feed/elution (7A) and hot feed/elution (7B) conditions.
Figure 7B:
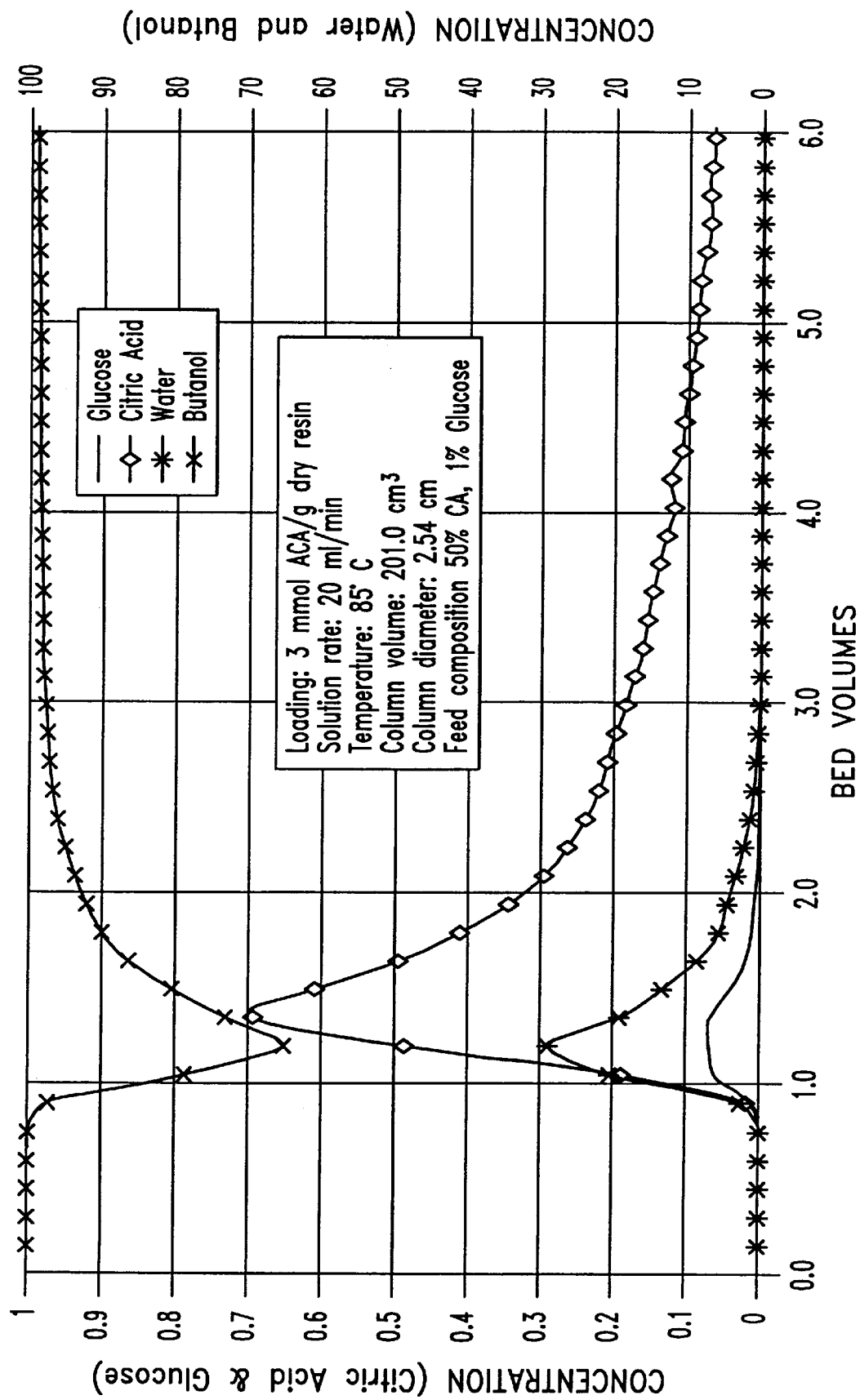

An aqueous citric acid/glucose product feed was treated over REILLEX™HP resin (30–60 mesh) in a jacketed column at a flow rate of 20 mL/min. using butanol as the eluent. For Example 7A, the feed and eluent temperatures were 25° C. For Example 7B, the feed and eluent temperatures were 85° C. The results are presented in respective FIGS. 7A and 7B. As shown in FIG. 7A, at relatively low temperatures a good separation of glucose and water on the one hand and citric acid on the other hand is exhibited. As shown in FIG. 7B, relatively high temperatures can be used to increase the peak citric acid concentration. Thus, the present invention employing relatively low temperatures during a separation phase and relatively high temperatures during a product recovery phase is applicable with advantage to this separation, while also dewatering the product feed and providing the recovered product substantially in alcohol. Such as product can, for example, be thereafter reacted so as to esterify the citric acid.

Example 8

Figure 8:
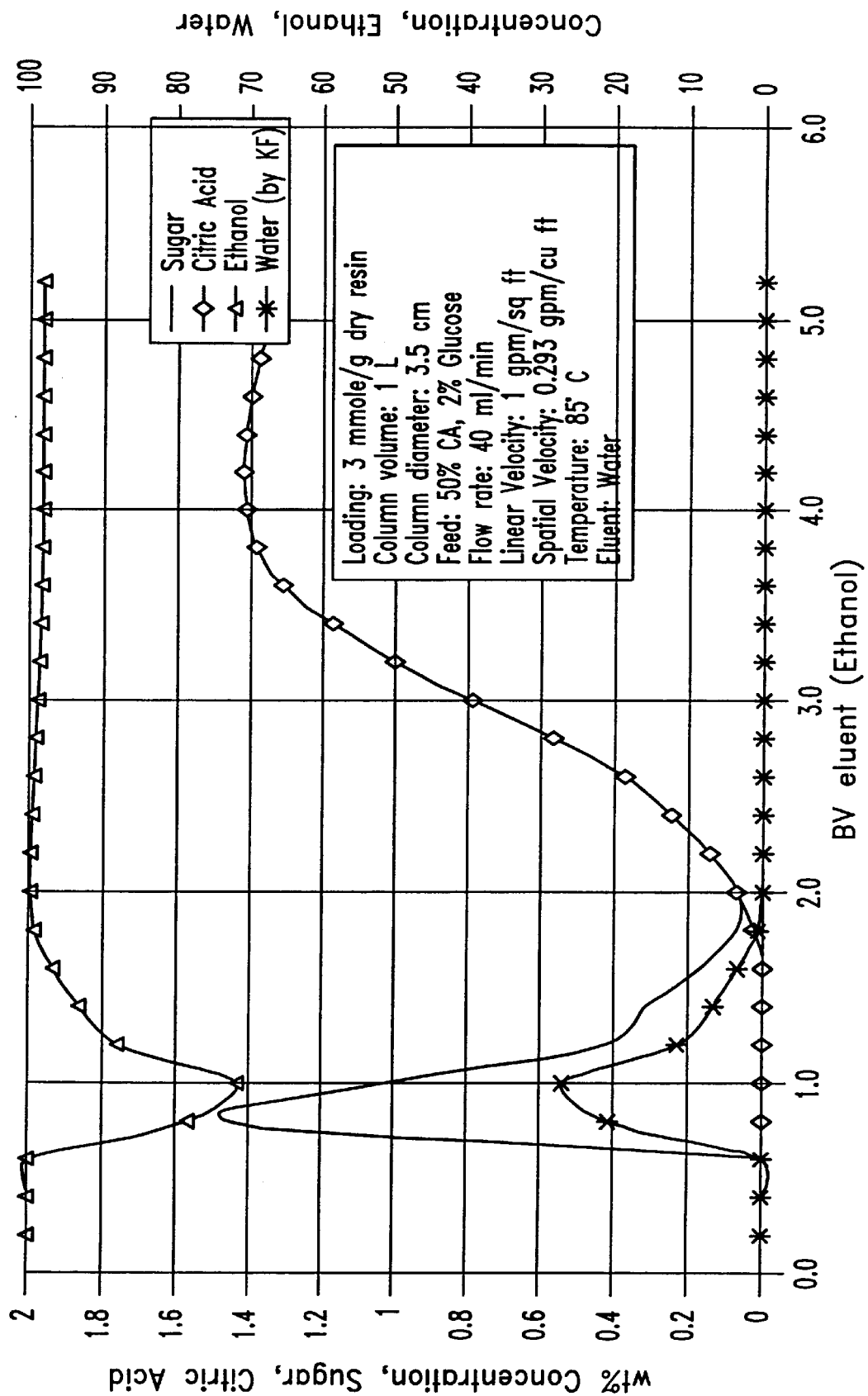
FIG. 8 is a graph showing an elution profile for an aqueous glucose/citric acid mixture chromatographically treated over REILLEX™HP crosslinked polyvinylpyridine polymer using ethanol as the eluent.

Example 7A was repeated except using ethanol as the eluent, and the results are presented in FIG. 8. These results show good separation of the citric acid from the water and glucose. Repeat of Example 7B except using ethanol as the eluent similarly shows an improved citric acid recovery profile but decreased separation. Thus, the applicability of thermally-assisted chromatography with ethanol to provide a dewatered, purified acid product is demonstrated.

Example 9

Figure 9:
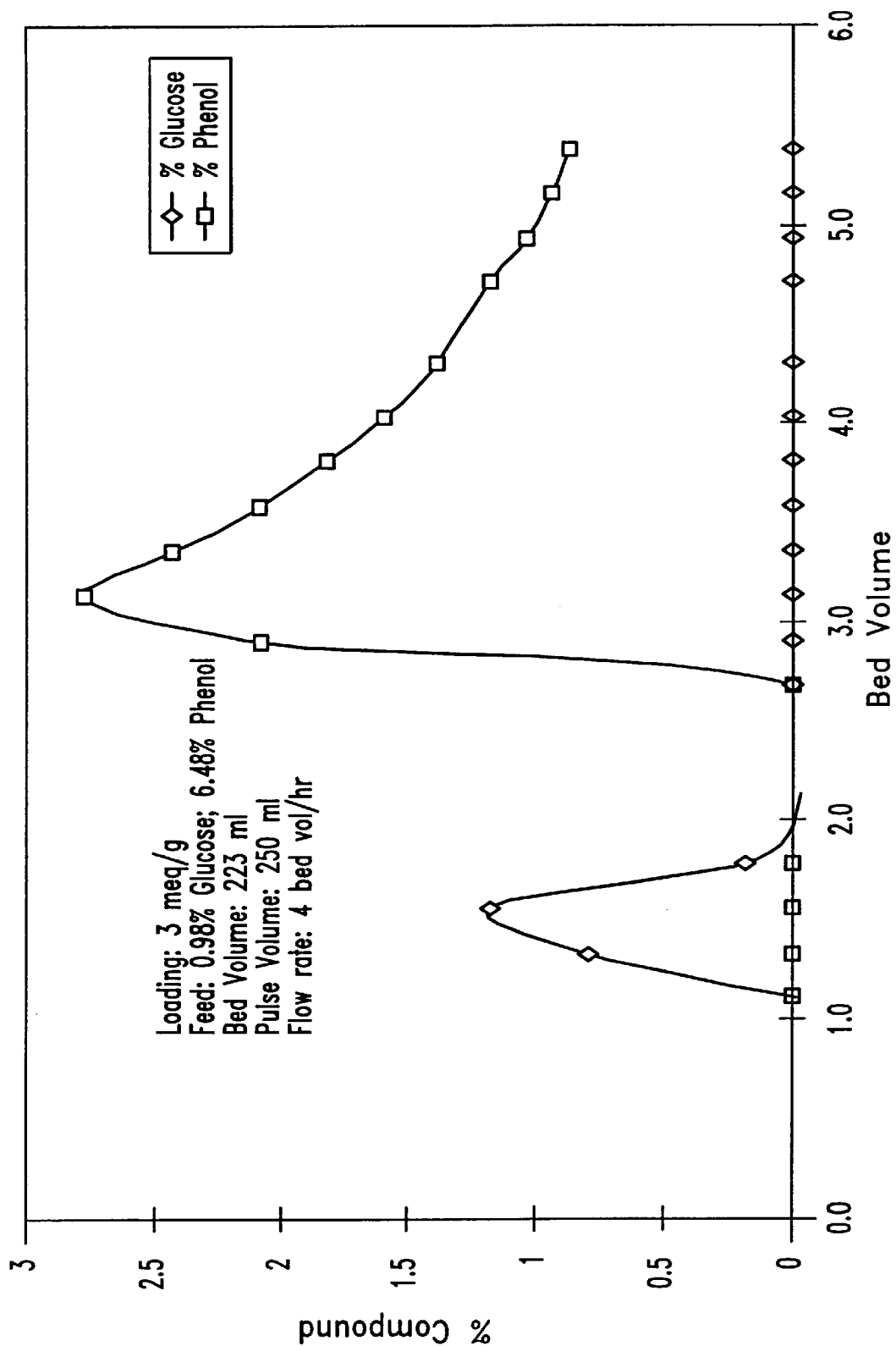
FIG. 9 is a graph showing an elution profile for an aqueous glucose/phenol mixture chromatographically treated over REILLEX™HP crosslinked polyvinylpyridine polymer under cold feed and hot elution conditions.

An aqueous 6.5% phenol/1% glucose product feed was treated over REILLEX™HP resin (30–60 mesh) in a jacketed column, using water as the eluent, under cold feed and hot eluent conditions generally as described in Example 2 above. The results are shown in FIG. 9 and demonstrate the applicability of thermally-assisted chromatography to the separation and recovery of phenol.

Example 10

Figure 11:
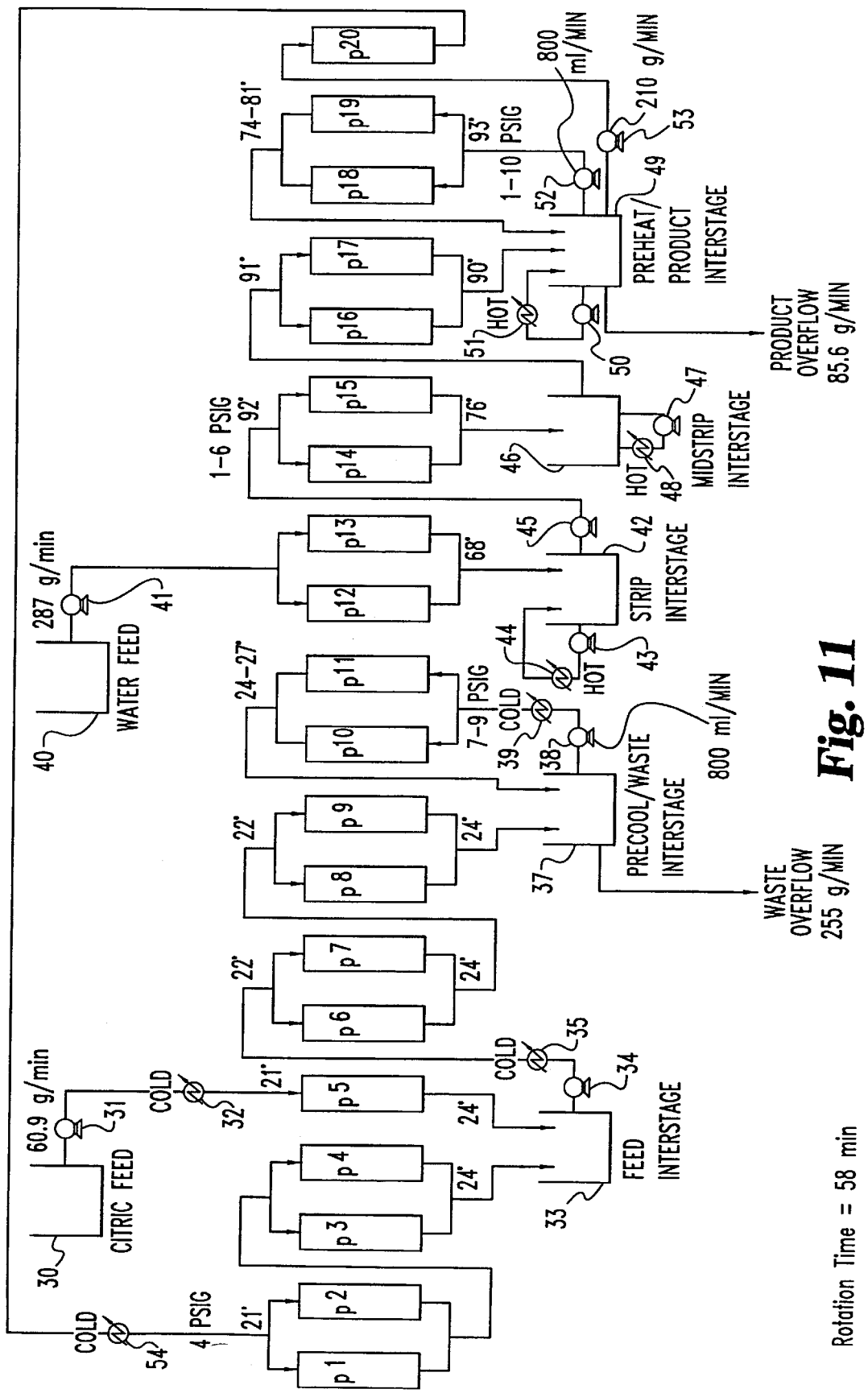
FIG. 11 is a schematic diagram illustrating a port configuration for a continuous contacting apparatus used in Example 10 below.

This run is presented for comparative purposes. FIG. 11 illustrates a configuration utilizing a CCA such as that described above. A run utilizing the configuration of FIG. 11 was carried out in an ISEP L100 pilot-scale CCA available from AST, Inc. The operation of the device is essentially as described above for CCA's, with the device having a stationary manifold with 20 ports and a carousel of 30 resin columns cooperating with the ports. The valving operation created isolates the columns from different fluid streams while maintaining continuous flow through the ports. The L100 pilot unit had glass columns (1 inch inner diameter, 350 ml volume), with polypropylene caps and 70 mesh screening to contain the resin. The upper and lower valve assemblies connected to the columns were constructed of polypropylene and 316 stainless steel. All connections throughout the apparatus were made with standard ¼ inch inner diameter polypropylene, polyethylene or Teflon tubing. The heat exchangers illustrated in FIG. 11 were either tube-and-shell or plate-and-frame heat exchangers. Low pressure steam was used for heating and chilled water (about 15° C.) or tap water (ambient temperature) was used for cooling. Peristaltic pumps with norprene tubing of various sizes (14–18) were used to transfer all solutions. The tubing was insulated in order to limit heat transfer with the surrounding environment.

Temperatures were measured in-line at the connection panel using ¼ inch stainless steel J-type thermocouples and recorded on a Yokogawa HR 1300 chart recorder. Pressures were measured in-line at the connection panel using stainless steel gauges. Flow rates were measure manually by weight over time (generally 30 minutes) at the various input or output ports.

Anhydrous USP/FCC grade citric acid, maltose monohydrate and anhydrous D-(+)-glucose, mixed anomers, and deionized water were used to make up the citric acid feed solutions. These solutions were prepared immediately prior to use to avoid potential bacterial growth.

REILLEX HP ™ polymer was obtained from Reilly Industries, Inc. in water wet form. The resin was sieved to obtain beads in a size range of 30–60 mesh. The resin was then soaked in 15% citric acid solution overnight and transferred to the L100 glass columns. Each column was backwashed with several bed volumes of water to remove fines, then connected to the L100. A total of 10.5 L of citric acid swollen resin was charged to the 30 columns, which equated to about 7.55 L of water swollen resin or 2.10 kg dry resin.

FIG. 11 shows a schematic diagram of a preferred port configuration in the L100 which was used in the citric acid run. The column rotation of the L100 was counter-current to solution flow, i.e. from right to left in FIG. 11. The measured temperatures, flow rates and insterstage tank positions are also shown in FIG. 11. Briefly describing the configuration, the flow pattern through the columns is generally downflow, with cold citric acid adsorption carried out in ports P5–P9, wash in ports P1–P4, and hot water desorption in ports P14–P17. Ports P10–P13 are used for cool-down of the resin after the desorption stage, while ports P18–Pl9 are used to preheat the loaded resins prior to the desorption stage. Port 20 is used to push remaining wash solution from the resin column.

More particularly, citric acid feed solution is fed from tank 30 using pump 31 through heat exchanger 32 (providing cooling) and into port P5. The stream exiting port P5 is fed to feed interstage tank 33. Solution from feed interstage tank 33 is fed using pump 34 through heat exchanger 35 (providing cooling) and into ports P6 and P7 in a parallel flow configuration. The streams exiting ports P6 and P7 is fed through heat exchanger 36 (providing cooling) and into ports P8 and P9 in parallel flow configuration. The streams exiting ports P8 and P9 are fed into precool/waste interstage tank 37. Solution from tank 37 is fed using pump 38 through heat exchanger 39 (providing cooling) and into ports P10 and P11, and the exit streams from ports P10 and P11 are directed back into tank 37. This "pump-around" provides precooling of the resin beds prior to their entry into the citric acid adsorption stage. Waste overflow also occurs at tank 37.

For the desorption stage, the desorption medium, e.g. water, was fed from feed tank 40 using pump 41 into ports P12 and P13 in parallel flow configuration. The exit streams from ports P12 and P13 flow into strip interstage tank 42. Pump 43 feeds solutions from tank 42 through heat exchanger 44 (providing heating) and back into tank 42. This pump-around through the heat exchanger heats the solutions in tank 42 for the desorption operations. It should be noted that strip interstage tank 42 and the other tanks employed in the configuration are preferably open to the atmosphere. This allows gasses evolved from the solutions, particularly when heated, to escape prior to entering the resin columns. This is advantageous for the reason that gasses flowing through the resin beds can cause channeling and interfere with the efficient operation of the device.

Heated solution from strip interstage tank 42 is fed using pump 45 into ports P14 and P15 in parallel flow. The exit streams from P14 and P15 are collected in midstrip interstage tank 46. Materials in tank 46 are also subjected to pump-around using pump 47 and heat exchanger 48 (providing heating). Materials from tank 46 are also fed to ports P16 and P17 in parallel flow configuration, and the corresponding exit streams are collected in preheat/product interstage tank 49. Materials in tank 49 are also subjected to pump-around using pump 50 and heat exchanger 51 (providing heating). A portion of the materials in tank 49 are recovered as product overflow. Another portion is fed using pump 52 into ports P18 and P19, and the corresponding exit streams are fed back into tank 49. The pump-around through P18 and P19 serves to preheat the resin beds prior to their entry into the desorption stages of the operation. Another portion of the materials in tank 49 is fed using pump 53 into port P20, which also preheats the resin beds at P20 to some extent.

In an important aspect of the present invention, the exit stream from port P20 is fed through heat exchanger 54 (providing cooling) and into the wash stage of the operation. Specifically, the port P20 exit stream is fed into ports P1 and P2 in parallel flow configuration. In the illustrated and preferred configuration, the product stream from port P20 serves exclusively as the wash agent in the wash operation. It will be understood, however, that this product stream could be used in conjunction with other wash agents fed to the wash stage, for example water. The collected exit streams from ports P1 and P2 are fed in parallel flow configuration into ports P3 and P4. Thus, in ports P1–P4, resin beds loaded with product, e.g. citric acid, are rinsed to remove non- or lesser-adsorbed materials such as sugars. The exit streams from ports P3 and P4 are collected in feed interstage tank 33, where they mix with the citric feed exiting port P5 and are processed along therewith as discussed beginning above.

In illustrative runs utilizing the configuration of FIG. 11, the L100 unit was run continuously for 3 hours before samples were collected, to facilitate the system reaching equilibrium or near equilibrium conditions prior to sampling. Output samples were collected over 30 minutes to ensure proper representation, and when more than one sample was taken, the time of collection was staggered with respect to the rotation rate so streams were not repeatedly coming from the same columns. In one such run, extending over 28 hours, a 14.7% citric acid feed containing 0.43% glucose and 2.03% maltose was fed to the system. The flow rates and temperatures of the flowing solutions at various key points in the system for this run are set out in FIG. 11. The product stream contained 9.73% citric acid on average (96% recovery) with 94% glucose and 97% maltose removal. In another similar run, except omitting the heat exchanger 32 and thus the cooling of the feed to column 5, the product stream contained 9.76% citric acid (98% recovery), and glucose and maltose removals were 96% and 98%, respectively.

Example 11

Figure 12:
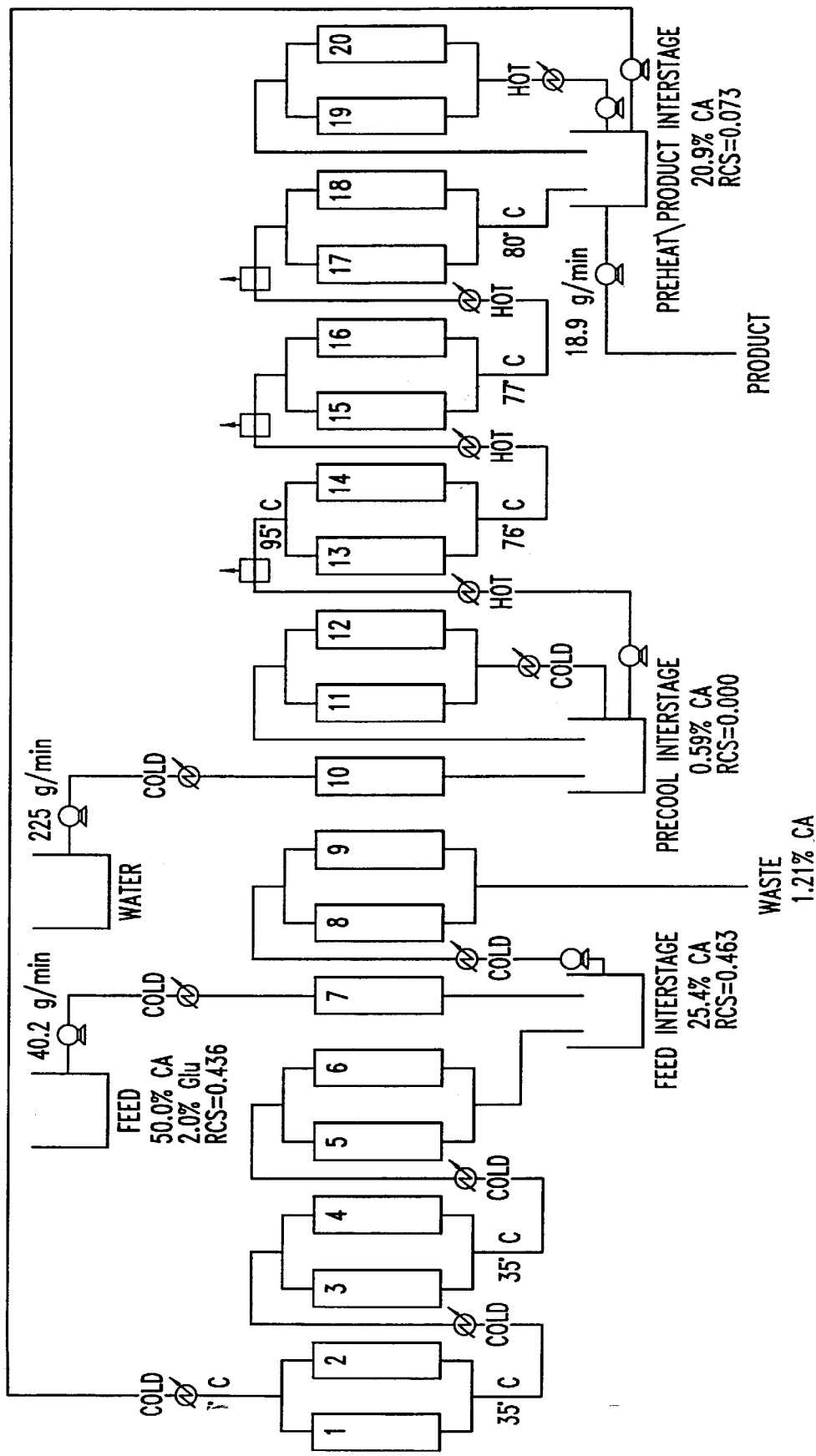
FIG. 12 is a schematic diagram illustrating a port configuration for a continuous contacting apparatus used in Example 11 below.

FIG. 12 provides a schematic diagram of an L100 configuration which can be used in processes of the present invention. This configuration is similar to that shown in FIG. 11, and thus common elements need not again be described. The configuration of FIG. 12, however, is arranged for advantageous conduct of processes employing thermally-managed chromatographic separation and elution, using product loadings substantially exceeding the effective capacity of the adsorbent. Comparing FIG. 12 to FIG. 11, one notes that the number of ports dedicated to a step in which a portion of the product stream is passed over previously product-loaded columns (ports P19–20 and P1–6) has been increased. This increase provides additional separation power, such that even at higher product loadings, impurities in the feed stream are removed from the column prior to the heated desorption stage (ports P13–P18). As in FIG. 11, measured temperatures and flow rates are shown in FIG. 12. Also shown in FIG. 12 are the concentrations of product (citric acid) and impurities in the various feeds/eluants in the process. Remarkably, as can be seen, using a feed of 50% citric acid having a readily carbonizable substance (RCS) level of 0.486, a product stream is recovered having a citric acid concentration of 20.9% and an RCS level of only 0.073. Thus, a product stream is obtained both highly rich in citric acid and low in RCS content. Moreover, the process described in conjunction with FIG. 12 has a much higher operating capacity than that with FIG. 11, with the latter operating at 1.3 milliequivalents of citric acid per gram of dry resin (meq/g dry resin), and the former operating at about 3 meq/g dry resin. This increase in operating capacity can be exploited to significantly reduce resin inventory and equipment size, leading to considerable improvements in throughput and process economics.

Example 12

Figure 13:
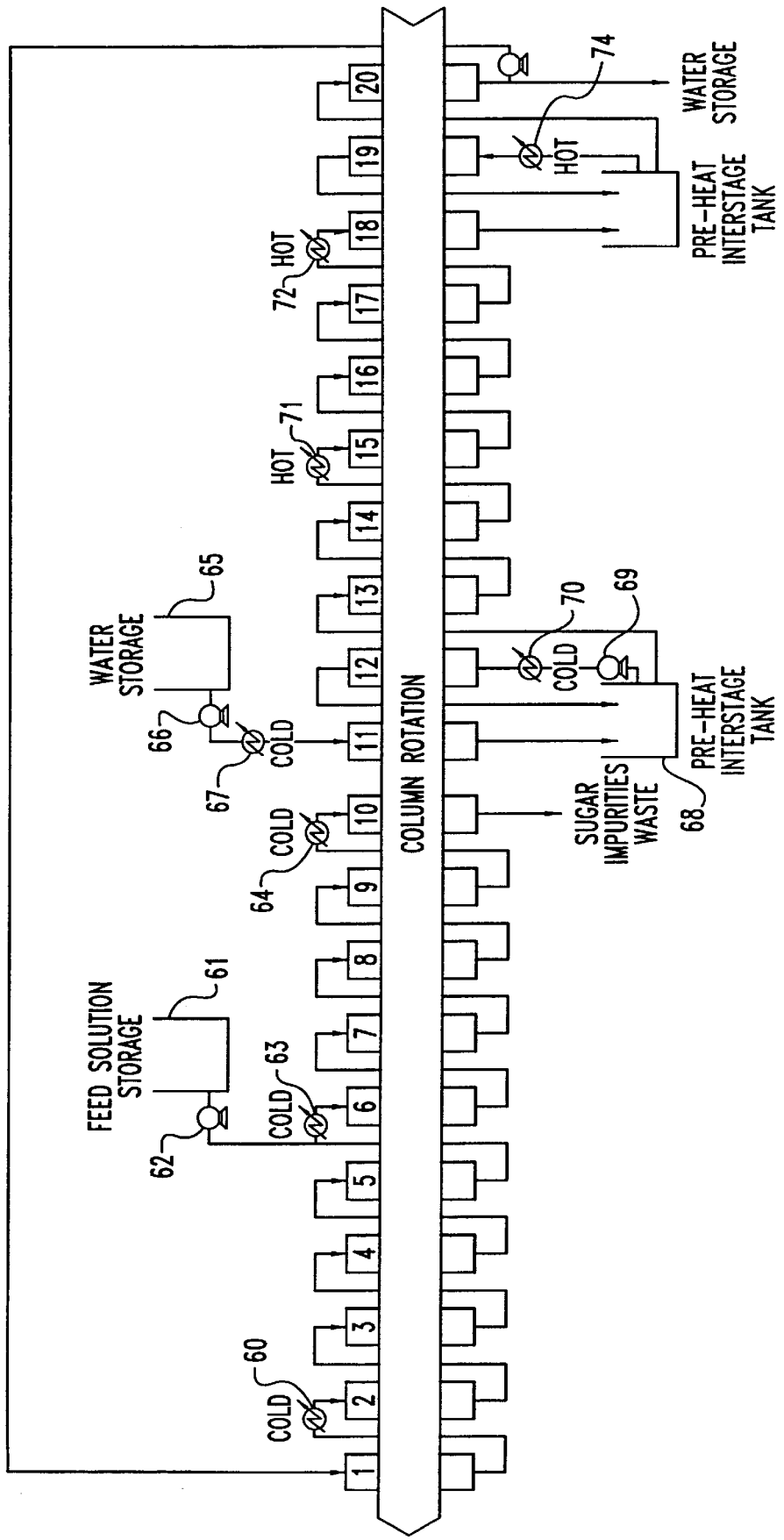
FIG. 13 is a schematic diagram illustrating a port configuration for a continuous contacting apparatus used in Example 12 below.

FIG. 13 provides a schematic diagram illustrating a port configuration which can be used in a CSEP device (also available from Advanced Separations Technologies, Inc.). This CSEP device is more optimal for chromatographic separations than the ISEP device described above, and contains 20 columns and 20 ports, with the columns being indexed sequentially past the ports. As can be seen in FIG. 13, the illustrative CSEP setup includes a generally counter-current, downflow arrangement, wherein parallel feed to ports (as occurs in the above-described ISEP configurations) is avoided so as to most effectively utilize the separation power of the resin inventory. The feed into port P1 is a portion of the acid-containing product stream from port P20 (discussed below). After exiting the column associated with port P1, this feed is passed through heat exchanger 60 providing cooling and then in counter current fashion through ports P2–P5. The stream is then combined with feed solution (e.g. containing 50% citric acid and sugar impurities) pumped from feed solution storage tank 61 by pump 62, and passed through heat exchanger 63 providing cooling, and into port P6. The solution is passed in counter-current mode through ports P7–P9, and thereafter through heat exchanger 64 providing cooling and into port P10. The stream exiting port P10 is relatively dilute in the product acid but concentrated in impurities (e.g. sugars), and is sent to waste.

Water or another liquid is pumped from storage tank 65 via pump 66 through heat exchanger 67 providing cooling, and into port P11. Exiting port P11 the stream is passed into pre-cool interstage tank 68. A portion of the solution in tank 68 is pumped via pump 69 through heat exchanger 70 providing cooling, and into Port P12 and back into tank 68. This pump around in port P12 cools the resin. Solution is also fed from tank 68 through ports P13–P14 in counter-current fashion, and then through heat exchanger 71 providing heating and into and through ports P15–P17 continuing in counter-current mode. The exit stream from P17 is passed through a further heat exchanger 72 providing heating, and through port P18 still in counter current. The exit stream from port P18 is feeds into pre-heat interstage tank 73. A portion of the solution in tank 73 is passed through heat exchanger 74 providing heating and upflow through port P19 and then fed back into tank 73. This pump around in port P19 heats the resin. A portion of the material in tank 73 is also passed downflow through port P20. The exit stream from P20 is a concentrated solution of the desired acid (e.g. citric acid), essentially free from the impurities (e.g. sugars) present in the original feed. A portion of this exit stream is collected as product, and another portion is fed to port P1, as discussed above.

The CSEP configuration of FIG. 13 can effectively process concentrated,. impurity-containing solutions of product acid (e.g. citric acid) even when fed at levels substantially exceeding the adsorption capacity of the solid adsorbent (e.g. REILLEX HP resin as described above) in the columns for the acid. In so doing, processes of the invention capitalize upon both chromatographic and traditional adsorption/thermal desorption phenomena, thereby significantly reducing adsorbent requirements for commercial processes and resulting in highly concentrated product fractions.

It will be understood that the port and other process configurations given in FIG. 13 are illustrative, and that other configurations can be used to implement the invention herein. For example, the number of columns dedicated to the separation or purification sections and the elution sections can be varied in accordance with process and/or product requirements. It is also possible to include a buffer zone utilizing one or more ports for example between ports P10 and P11 in FIG. 13. Moreover, it will be readily understood that the location of the heat exchangers (providing heating or cooling) in the operation can be altered while practicing the invention.

Example 13

Figure 14:
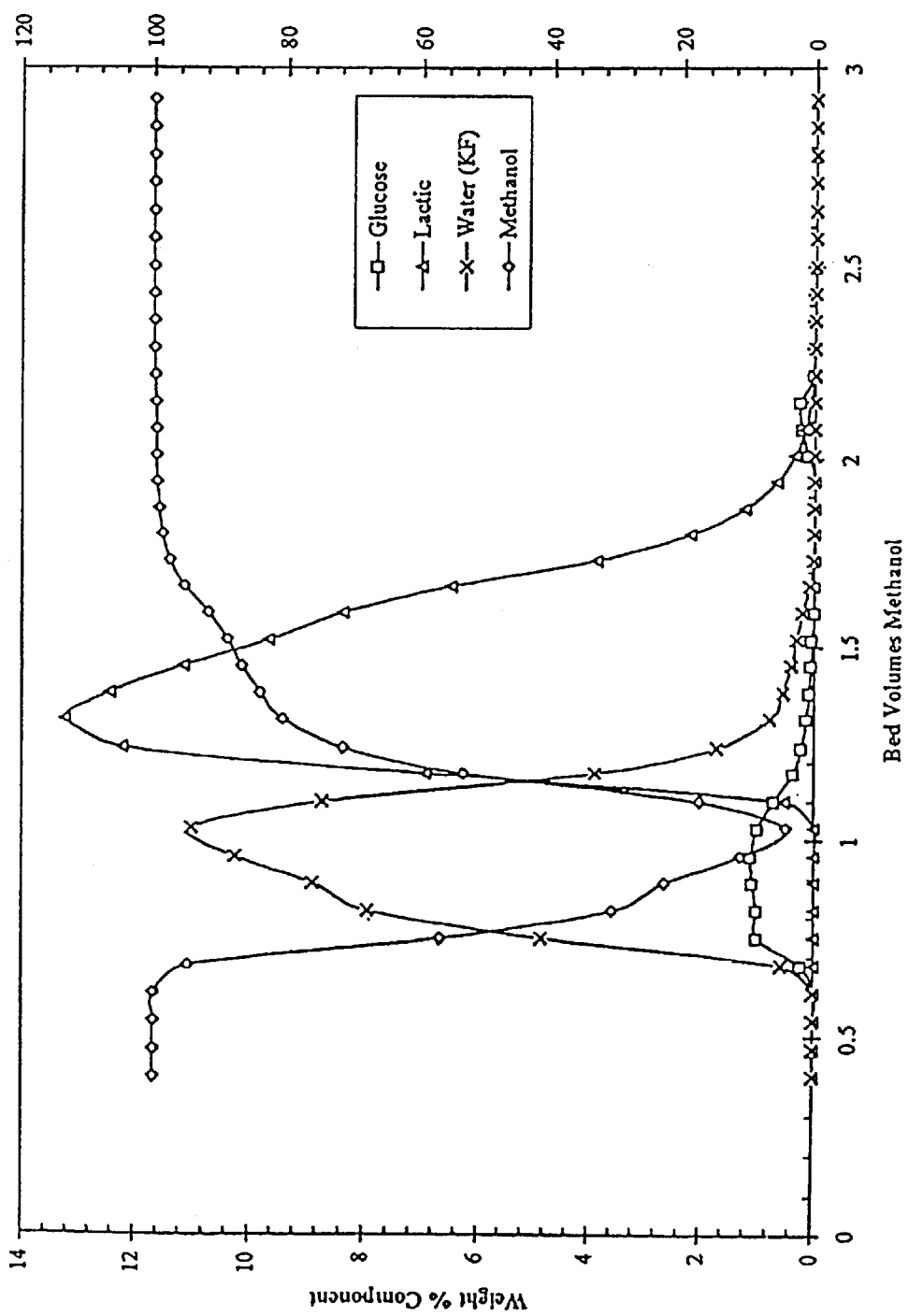
FIG. 14 is a graph showing an elution profile for an aqueous lactic acid solution chromatographically treated over REILLEX™HP crosslinked polyvinylpyridine polymer under isothermal conditions using methanol as the eluent.

A glass column (5.8 cm I.D.×75 cm) was packed with 1500mL of REILLEX HP resin, conditioned with water to remove air, and the water displaced with methanol. A 13% by weight aqueous lactic acid solution containing 1.29% glucose was pumped onto the column and immediately eluted with methanol at a rate of 100 ml/min. The run was carried out at 25° C. Samples of effluent were collected and analyzed to produce a plot of concentration of each component vs. bed volume of eluent fed. The results are shown in FIG. 14, and demonstrate that the lactic acid was separated from the glucose and substantially all of the water, providing a major cut of relatively highly concentrated lactic acid in methanol. It was thereby demonstrated that chromatographic dewatering processes with an alcohol eluent provide highly desirable lactic acid elution profiles even when run under isothermal conditions. Thus, aqueous solutions of lactic acid or other similarly weak acids such as acetic can be advantageously treated under isothermal conditions in a CCA flow configuration such as that shown in FIGS. 12 and 13, to dewater and recover the acid in high concentration in an alcohol solvent.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

All publications cited herein are indicative of the level of skill in the art and are hereby incorporated by reference as if each had been individually incorporated by reference and fully set forth.

What is claimed is:

1. A process for the dewatering and recovery of an organic acid product from an aqueous solution, comprising chromatographically treating the aqueous solution of acid product over an adsorbent resin having a capacity for the acid product, the treating using an alcohol as a mobile phase under conditions wherein the acid product is eluted in an alcohol solution substantially free from water, said chromatographically treating including (a) providing said acid at a level which exceeds the capacity of the adsorbent resin and (b) passing said aqueous solution and said alcohol together over said adsorbent resin.

2. A process for dewatering an organic acid comprising:

providing a contacting zone containing an adsorbent having a capacity for the acid and exhibiting higher affinity for the acid than water;

introducing an aqueous solution of the acid into the contacting zone; said acid provided at a level which exceeds the capacity of the adsorbent for said acid;

passing a liquid alcohol through the contacting zone together with said aqueous solution under conditions which are effective to establish a front of the organic acid separated in the contacting zone from a front of the water;

eluting the front of organic acid from the contacting zone to provide an eluant containing the organic acid in solution in the alcohol, said eluate being substantially free from water.

3. A chromatographic process for dewatering an organic acid product, comprising:

(a) providing a plurality of contacting zones containing an adsorbent which has a capacity for the acid product and which exhibits a higher affinity for the acid product than for water;

(b) sequentially processing said contacting zones through a chromatographic separation zone wherein an alcohol eluent solution and an aqueous solution containing the acid are together passed through the contacting zones to achieve a chromatographic process in which the acid is separated from the water, said aqueous solution being passed through the contacting zones to provide a level of acid product which exceeds the capacity of the adsorbent for the acid product; and (c) after step (b), sequentially processing the contacting zones through an elution zone so as to elute the acid product from the one or more contracting zones in a solution of the alcohol which is substantially free from water.

4. The process of claim 1, 2 or 3, wherein the acid is a carboxylic acid.

5. The process of claim 4 wherein the carboxylic acid is lactic acid.

6. The process of claim 4 wherein the alcohol is selected from the group consisting of methanol, ethanol, propanol, isopropanol, butanol and methylisobutyl carbinol.

7. The process of claim 4 wherein the solution of alcohol contains no more than 5% by weight of water.

\* \* \* \* \*